US005747661A

United States Patent [19]
Evans et al.

[11] Patent Number: 5,747,661
[45] Date of Patent: May 5, 1998

[54] RETINOID-INDUCIBLE RESPONSE ELEMENTS

[75] Inventors: Ronald M. Evans, La Jolla, Calif.;
David J. Mangelsdorf, Duncanville;
Patricia J. Willy, Dallas, both of Tex.

[73] Assignee: Howard Hughes Medical Institute, Chevy Chase, Md.

[21] Appl. No.: 373,935

[22] Filed: Jan. 13, 1995

[51] Int. Cl.$^6$ .................................................. C12N 15/85
[52] U.S. Cl. ........................... 536/24.1; 435/6; 435/7.1; 435/7.21; 435/325; 530/402; 536/23.1
[58] Field of Search ............................ 435/6, 7.1, 7.21, 435/325; 530/402; 536/24.1

[56] References Cited

FOREIGN PATENT DOCUMENTS 0 173 378  3/1986  European Pat. Off. .

OTHER PUBLICATIONS

Allegretto et al., "Transactivation Properties of Retinoic Acid and Retinoid X Receptors in Mammalian Cells and Yeast" *J. Biol. Chem.* 268:26625–26633 (1993).

Amy et al., "Molecular cloning of the mammalian fatty acid synthase gene and identification of the promoter region" *Biochem. J.* 271:675–679 (1990).

Apfel et al. "A Novel Orphan Receptor Specific for a Subset of Thyroid Hormone–Respnsive Elements and Its Interaction with the Retinoid/Thyroid Hormone Receptor Subfamily" *Mol. Cell Biol.* 14:7025–7035 (1994).

Kastner and Chambon, "Role of Nuclear Retinoic Acid Receptors in the Regulation of Gene Expression" *BOOK–Vitamin A in Health & Disease* cd. R. Blomhoff pp. 189–238 Marcel Dekker, Inc. (1994).

Devereux et al., "A comprehensive set of sequence analysis programs for the VAX" *Nucleic Acids Res.* 12:387–395 (1984).

Fields and Song, "A novel genetic system to detect protein–protein interactions" *Nature* 340:245–246 (1986).

Giguere, "Retinoic Acid Receptors and Cellular Retinoid Binding Proteins: complex Interplay in Retinoid Signaling" *Endocr. Rev.* 15:61–79 (1994).

Giguere, et al. "Functional Domains of the Human Glucocorticoid Receptor" *Cell* 46:645–652 (1986).

Giguere, et al., "Identification of a receptor for the morphogen retinoic acid" *Nature* 330:624–629 (1987).

Heery, et al., "Efficient transactivation by retinoic acid receptors in yeast requires retinoid X receptors" *Proc. Natl. Acad. Sci. USA* 90:4281–4285 (1993).

Heyman, et al., "9–Cis Retinoic Acid Is a High Affinity Ligand for the Retinoid X Receptor" *Cell* 68:397–406 (1992).

Hollenberg and Evans, "Multiple and Cooperative Trans–Activation Domains of the Human Glucocorticoid Receptor" *Cell* 55:899–906 (1988).

Hollenberg et al., "Primary structure and expression of a functional human glucocorticoid receptor cDNA" *Nature* 318:635–641 (1985).

Izumo and Mahdavi, "Thyroid hormone receptor α isoforms generated by alternative splicing differentially activate myosin HC gene transcription" *Nature* 334:539–542 (1988).

Kang et al., "Wild Type GAL–4 Binds Cooperatively to the GAL1–10 UAS$_G$ in Vitro" *J. Biol. Chem.* 268:9629–9635 (1993).

Kastner et al., "Genetic Analysis of RXRα Developmental Function: convergence of RXR and RAR Signaling Pathways in Heart and Eye Morphogenesis" *Cell* 78:987–1003 (1994).

Kliewer et al., "Convergence of 9–cis retinoic acid and peroxisome proliferator signalling pathways through heterodimer formation of their receptors" *Nature* 358:771–774 (1992).

Kliewer et al., "Retinoid X receptor interacts with nuclear receptors in retinoic acid, thyroid hormone and vitamin $D_3$ signalling" *Nature* 355:446–449 (1992).

Koelie et al., "The Drosophila EcR Gene Encodes an Ecdysone Receptor, a New Member of the Steroid Receptor Superfamily" *Cell* 67:59–77 (1991).

Kurokawa et al., "Differential orientations of the DNA–binding domain and carboxy–terminal dimerization interface regulate binding site selection by nuclear receptor heterodimers" *Genes & Dev.* 7:1423–1435 (1993).

Kurokawa et al., "Regulation of retinoid signalling by receptor polarity and allosteric control of ligand binding" *Nature* 371:528–531 (1994).

Leid et al., "Purification, Cloning, and RXR Identity of the HeLa Cell Factor with Which RAR or TR Heterodimerizes to Bind Target Sequences Efficiently" *Cell* 68:377–395 (1992).

Levin et al., "9–Cis retinoic acid stereoisomer binds and activates the nuclear receptor RXRα" *Nature* 355:359–361 (1992).

Mangelsdorf et al., "Nuclear receptor that identifies a novel retinoic acid response pathway" *Nature* 345:224–229 (1990).

Mangelsdorf et al., "A Direct Repeat in the Cellular Retinol–Binding Protein Type II Gene Confers Differential Regulation by RXR and RAR" *Cell* 66:555–561 (1991).

Mangelsdorf et al., "The Retinoid Receptors" *BOOK–The Retinoids* pp. 319–149 (1994).

(List continued on next page.)

*Primary Examiner*—John Ulm
*Assistant Examiner*—Kenneth A. Sorensen
*Attorney, Agent, or Firm*—Stephen E. Reiter; Gray Cary Ware & Freidenrich

[57] ABSTRACT

The characterization of LXRα, an orphan member of the nuclear hormone receptor superfamily that can function as a tissue-specific mediator of 9-cis retinoic acid (9cRA) is described herein. When expressed in cells, LXRα activates transcription in response to 9cRA on a distinct response element, termed an LXRE. Significantly, neither RXR homodimers nor RXR/RAR heterodimers are able to substitute for LXRα in mediating this retinoid response. The LXRα response to retinoids is due to its unique interaction with endogenous RXR. This interaction shifts RXR from its previously described role as a silent, heterodimer partner to an active ligand binding partner, thus defining a novel retinoid response pathway.

5 Claims, 15 Drawing Sheets

OTHER PUBLICATIONS

Mangelsdorf et al., "Characterization of three RXR genes that mediate the action of 9-cis retinoic acid" *Genes & Dev.* 6:329–344 (1992).

Marks, et al., "H-2RIIBP (RXRβ) heterodimerization provides a mechanism for combinatorial diversity in the regulation of retinoic acid and thyroid hormone responsive genes" *EMBO J.* 11:1419–1435 (1992).

Nagpal et al., "RARs and RXRs: evidence for two autonomous transactivation functions (AF-1 and AF-2) and heterodimerization in vivo" *EMBO J.* 12:2349–2360 (1993).

Nagpal et al., "Promoter Context—and Response Element-Dependent Specificity of the Transcriptional Activation and Modulating Functions of Retinoic Acid Receptors" *Cell* 70:1007–1019 (1992).

Perlmann et al., "Determinants for selective RAR and TR recognition of direct repeat HREs" *Genes & Dev.* 7:1411–1422 (1993).

Sadowski and Ptashne, "A vector for expressing GAL4 (1–147) fusions in mammalian cells" *Nucleic Acids Res.* 17:7539.

Song et al., "Ubiquitous receptor: A receptor that modulates gene activation by retinoic acid and thyroid hormone receptors" *Proc. Natl. Acad. Sci. USA* 91:10809–10813 (1994).

Sucov et al., "Characterization of an autoregulated response element in the mouse retinoic acid receptor type β gene" *Proc. Natl. Acad. Sci. USA* 87:5392–5396 (1990).

Sucov et al., "RXRα mutant mice establish a genetic basis for vitamin A signaling in heart morphogenesis" *Genes & Dev.* 8:1007–1018 (1994).

Titcomb et al., "Sensitive and Specific Detection of Retinoid Receptor Subtype Proteins in Cultured Cell and Tumor Extracts" *Mol. Endicrinol.* 8:870–877 (1994).

Triezenberg et al., "Functional dissection of VP16, the trans-activator of herpes simplex virus immediate early gene expression" *Genes & Dev.* 2:718–729 (1988).

Umesono et al., "Direct Repeats as Selective Response Elements for the Thyroid Hormone, Retinoic Acid, and Vitamin $D_3$ Receptors" *Cell* 65:1255–1266 (1991).

Weinberger et al., "The c-erb-A gene encodes a thyroid hormone receptor" *Nature* 324:641–646 (1986).

Yu et al., "RXRβ: A Coregulator That Enhances Binding of Retinoic Acid, Thyroid Hormone, and Vitamin D Receptors to Their Cognate Response Elements" *Cell* 67:1251–1266 (1991).

Zhang et al., "Homodimer formation of retinoid X receptor induced by 9-cis retinoic acid" *Nature* 358:587–591 (1992).

Zhang et al., "Retinoid X receptor is an auxiliary protein for thyroid hormone and retinoic acid receptors" *Nature* 355:441–446 (1992).

Willy et al., "LXR, a nuclear receptor that defines a distinct retinoid response pathway" *Genes and Development* 9:1033–1045 (1995).

DeJong et al, (1988) *J. Biol-Chem.* 263:8430–8436.

RETINOID-INDUCIBLE RESPONSE ELEMENTS

This invention was made with Government support under Grant No. NIDDK 1 R55 DK45657-01, awarded by the National Institutes of Health. The Government has certain rights in the invention.

FIELD OF THE INVENTION

The present invention relates to intracellular receptors, and methods for the modulation thereof. In a particular aspect, the present invention relates to novel heterodimeric complexes. In another aspect, the present invention relates to methods for modulating processes mediated by retinoid X receptor and/or orphan receptor LXR.

BACKGROUND OF THE INVENTION

All-trans retinoic acid (atRA) and 9-cis retinoic acid (9cRA) are metabolites of vitamin A that mediate tissue specific expression of target genes. This is accomplished through binding to two classes of nuclear hormone receptors, the retinoic acid receptors (RARs) and retinoid X receptors (RXRs; reviewed by Mangelsdorf et al., in *The retinoids* Sporn et al., eds. (New York, Raven Press) 319–349 (1994); and by Kastner et al., in *Vitamin A in health and disease*, R. Blomhoff, ed. (New York: Marcel Dekker, Inc.) 189–238 (1994)). 9cRA is a high affinity ligand for both RARs and RXRs, whereas atRA is a ligand for only RARs. Like other members of the nuclear receptor superfamily, the retinoid receptors transactivate their target genes by binding to specific sites called hormone response elements found within the 5', regulatory region of the target gene.

The highest affinity hormone response elements for the retinoid receptors, as well as the vitamin D receptor (VDR), thyroid hormone receptors (TRs), and peroxisome proliferator activated receptors (PPARs) have been characterized as direct repeats (DRs) of the canonical hexad, AGGTCA, separated by one to five nucleotides (reviewed by Mangelsdorf et al., 1994, supra and Giguère, V., in *Endocr. Rev.* 15:61–79 (1994)). RAR, VDR, TR and PPAR preferentially bind to their hormone response elements in vitro as heterodimers complexed with RXR. Reconstitution studies in yeast (see Heery et al., in *Proc. Natl. Acad. Sci. USA* 90:4281–4285 (1993); and Allegretto et al., in *J. Biol. Chem.* 268:26625–26633 (1993)) and RXR gene disruption experiments in mice (see Sucov et al., in *Genes Dev.* 8:1007–1018 (1994); and Kastner et al., in *Cell* 78:987–1003 (1994)) confirm the function of the RXR heterodimer and suggest that it has an obligatory role in vivo as well as in vitro. Thus, RXRs appear to be essential pleiotropic regulators of several signaling pathways.

In terms of retinoid signaling, two distinct pathways are known, the RXR/RAR heterodimer and RXR homodimer. The RXR/RAR heterodimer mediates atRA or 9cRA action through its high affinity binding to a direct repeat response element having a spacer of 5 nucleotides (i.e., a DR5 element), and to some extent DR2 elements. Recently, it has been shown that when the RXR/RAR heterodimer is bound to DNA, RXR occupies the 5– half-site and RAR occupies the 3' half-site of the DR5 element (see Perlmann et al., in *Genes Dev.* 7:1411–1422 (1993); and Kurokawa et al., in *Genes Dev.* 7:1423–1435 (1993)). In this configuration, RXR is unable to bind ligand and thus functions as a silent partner (Kurokawa et al., in *Nature* 371:528–531 (1994)). The role of RXR as a silent partner is consistent with the finding that other receptors that heterodimerize with RXR do not require 9cRA for their activation (see, for example, Yu et al., in *Cell* 67:1251–1266 (1991); Kliewer et al., in *Nature* 355:446–449 (1992); Zhang et al., in *Nature* 355:441–446 (1992); Marks et al., in *EMBO J.* 11:1419–1435 (1992); Leid et al., in *Cell* 68:377–395 (1992); and Kliewer et al., in *Nature* 358:771–774 (1992)).

In the RXR homodimer, RXR acts as its own partner and mediates 9cRA action through binding to DR1 elements. Interestingly, the RXR/RAR heterodimer also binds the DR1 element, and does so with higher affinity than the RXR homodimer. The consequence of this binding is that the RXR/RAR heterodimer is a potent repressor of 9cRA activation through the RXR homodimer (Mangelsdorf et al., in *Cell* 66:555–561 (1991); Kurokawa et al., 1994, supra). These findings suggest that in order for the RXR homodimer to be active (i.e., for RXR to be able to function in vivo as a 9cRA receptor), the ratio of RXR to RAR in a cell must be very high. This may explain why cells that endogenously express RXR and RAR (even at low levels) yield significant retinoid responses with DR5-containing reporter genes, but do not yield any response with DR1-containing reporter genes, unless RXRs are overexpressed in these cells (see Mangelsdorf et al., 1991, supra). Given the ubiquitous expression pattern of RARs and RXRs, it is of interest to determine whether 9cRA activation of RXR occurs only through DR1 elements, or whether any other pathways exist for mediating a 9cRA-RXR response.

BRIEF DESCRIPTION OF THE INVENTION

In accordance with the present invention, we have discovered that an orphan member of the nuclear receptor superfamily, named LXRα (see SEQ ID NO:1), in the presence of RXR ligand (e.g., 9cRA), is a potent inducer of transactivation through a distinct retinoid response element. The LXRα response to retinoids is due to the unique interaction of LXRα with endogenous RXR in cells. This interaction permits RXR to work as an active, ligand-binding heterodimeric partner. These results demonstrate the ability of LXRα to function as a tissue-specific mediator of a novel retinoid-responsive pathway.

BRIEF DESCRIPTION OF THE FIGURES

In FIG. 3C, ligands were added as described with reference to FIG. 2. Luciferase activity is expressed as RLUs (relative light units) corrected for transfection efficiency using an internal μgal standard and represents the mean of triplicate assays (±SEM).

DETAILED DESCRIPTION OF THE INVENTION

Figure 6:
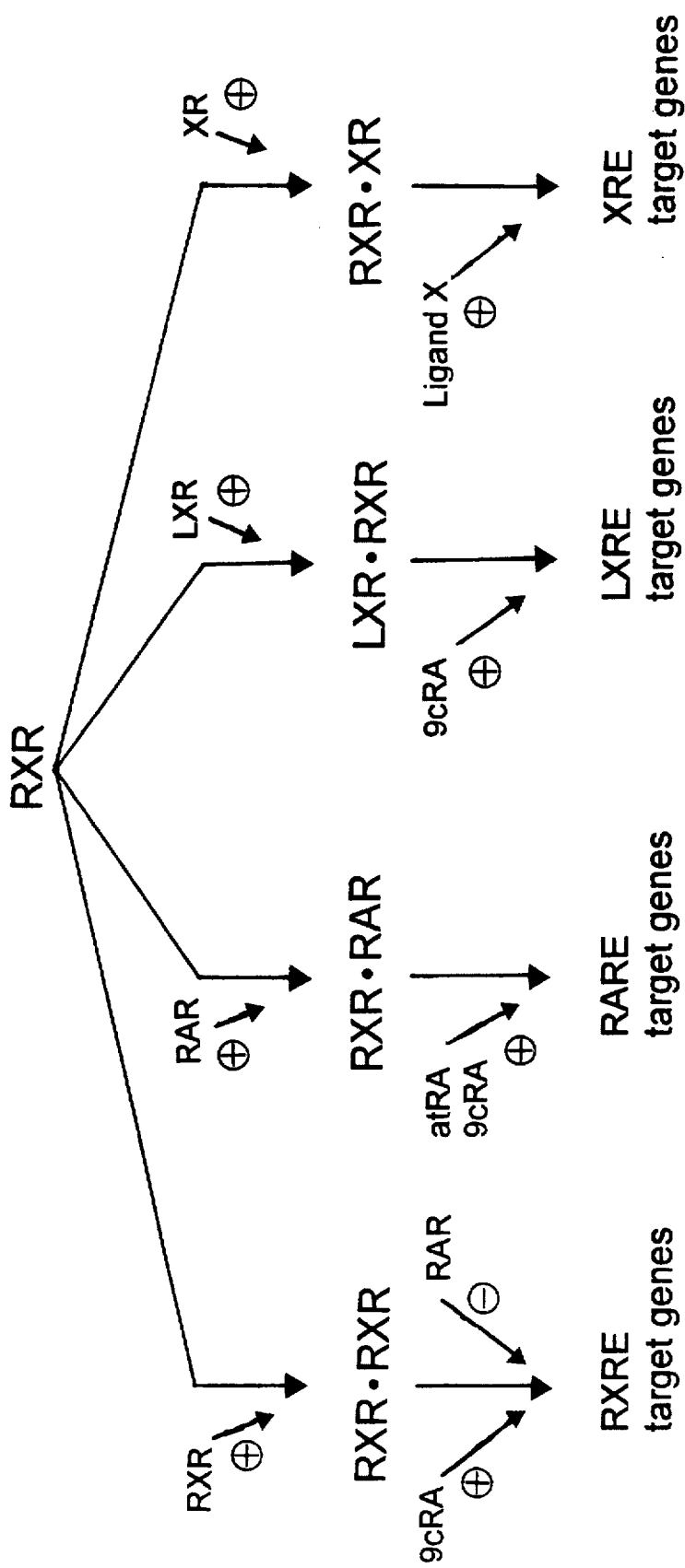
FIG. 6 summarizes the multiple RXR signaling pathways. As a dimer partner, RXR is a master regulator of multiple hormone response pathways, including at least three that are retinoid responsive: (1) The RXR homodimer binds and is responsive to 9cRA on DR1 target gene elements (RXREs). This response is strongly repressed by RAR, which preferentially heterodimerizes with RXR. The interaction with RAR prevents RXR from binding ligand and forms a high affinity complex on the RXRE that is transcriptionally inactive. Thus, in order for RXR to respond to ligand, the ratio of RXR to RAR in a cell must be very high. (2) As a heterodimer, RXR does not bind ligand, but functions as a silent partner to RAR in mediating atRA and 9cRA responses through RAREs composed of DR5 (and presumably DR2) sequences. (3) As described herein, the orphan receptor LXRα defines a third 9cRA response pathway in which RXR participates as the active ligand binding partner. The LXR/RXR heterodimer responds to retinoid through a specific DR4-like element (the LXRE). Unlike the RXR response on a DR1 element, the LXR/RXR response is uniquely sensitive to 9-cRA and can function potently in the presence of the low levels of endogenous RXR in the cell. (4) Finally, RXR subserves the role of heterodimeric partner to several receptor systems (designated by XR), including vitamin D, thyroid hormone, and peroxisome proliferators.

RXRs are unique in their ability to function as both homodimeric receptors and as obligate heterodimeric partners to receptors in multiple hormone response pathways. The central role of RXR in these pathways is summarized in FIG. 6. In the retinoic acid response pathway, where RXR is present as part of a heterodimer, RXR does not bind ligand, but rather serves as a cofactor to RAR in preferentially activating target genes containing DR5 response elements. As a homodimer, the ability of RXR to bind ligand and function exclusively as a 9cRA receptor is limited to DR1-containing target genes.

Up until the present invention, activation through the RXR homodimer has been observed to be dependent on the artificial overexpression of RXR, since in all cell types tested the ubiquitous endogenous expression of RAR and RXR leads to the preferential formation of heterodimers that prevent RXR from binding ligand. This apparent lack of target cells in which the expression of RAR is sufficiently lower than RXR to allow formation of RXR homodimers raises the question of how RXR functions in vivo as a 9cRA receptor. In order for RXR to function in vivo as a 9cRA receptor, it was suspected that an alternative pathway exists that allows RXR to so function. Indeed, in accordance with the present invention, the orphan receptor LXRα has been identified as a cofactor that permits RXR to function as a potent 9cRA receptor with a distinct target gene specificity. The LXR effect is mediated through a unique heterodimeric interaction, which switches the role of RXR from a silent partner to an active, ligand-binding partner in the heterodimer complex. Significantly, this finding establishes a new pathway by which RXR can function as a bona fide receptor and further, it defines a third retinoid response system with a novel target gene specificity.

Unlike the RXR homodimer, the LXR/RXR heterodimer response to 9cRA in cells can occur in the presence of endogenous RXR and RAR. In the context of the LXR heterodimer, the mechanism of RXR activation by ligand appears similar to that of RAR: both receptors require a partner for specific DNA binding and ligand activation. The nature of the LXR heterodimer, however, is unique in several respects. The heterodimerization of LXR and RXR is specific, as no evidence of an LXR interaction with other receptors has been found. Furthermore, while the LXR/RXR heterodimer binds to a variety of DR4-like response elements, it is only ligand responsive on the LXRE. This finding indicates that DNA binding alone is not sufficient for ligand inducibility.

One fundamental question in the field of nuclear hormone receptors is the function of the ever increasing subclass of this protein family that have been referred to as orphan receptors. Although initially activators for these potential ligand-dependent transcription factors are unknown, their remarkable similarity to other nuclear receptors suggests that they may have ligands and operate in a fashion similar to the known receptors. Indeed, studies on both the known and orphan receptors have revealed that many of these proteins have transcription modulating activity that may be considered ligand-independent. As previously demonstrated for RXR and as shown here for LXR, these receptors can serve important ligand-independent functions as obligate heterodimer partners. Based on these findings, it can be predicted that other orphan receptors exist that serve similar roles, some of which are likely to intersect the retinoid response system.

In accordance with the present invention, there are provided retinoid-inducible response elements having the sequence:

5'-GGTTTA-NNNN-AGTTCA (SEQ ID NO:2), wherein each N is independently selected from A, G, T or C. Optionally, the above-described retinoid-inducible response element can have additional 3' residues, $N_1N_2$, wherein $N_1$ is selected from A or T, and $N_2$ is selected from C or G (SEQ ID NO:3).

A presently preferred retinoid-inducible response element of the invention has the sequence:

5'-GGTTTA-AATA-AGTTCA (SEQ ID NO:4), optionally having additional 3' residues, $N_1N_2$, as defined hereinabove (SEQ ID NO:5).

An especially preferred retinoid-inducible response element of the invention has the sequence:

5'-CTTGCGGTTCCCAG-GGTTTA-AATA-AGTTCA (SEQ ID NO:6), optionally having additional 3' residues, $N_1N_2$, as defined hereinabove (SEQ ID NO:7).

In accordance with another embodiment of the present invention, there is provided a method to render RXR-containing cells responsive to RXR selective ligands, said method comprising contacting said cells with at least one isoform of LXR. This method is particularly effective when using cells which further contain members of the steroid/thyroid superfamily with which RXR forms heterodimers, e.g., RAR, VDR, TR, PPAR, and the like.

As employed herein, the phrase "isoform of LXR" refers to any orphan receptor that by sequence comparison is related to LXRα described herein. Thus, isoforms of LXR includes the receptor described by Apfel et al., in *Mol. Cell. Biol.* 14:7025–7035 (1994), the receptor described by Song et al., in *Proc. Natl. Acad. Sci. USA* 91:10809–10813 (1994), and the like.

In accordance with yet another embodiment of the present invention, there is provided a method to alter the target gene specificity of RXR-containing cells, said method comprising contacting said cells with at least one isoform of LXR.

In accordance with still another embodiment of the present invention, there is provided a method to activate, in RXR-containing cells, target gene(s) operatively associated with response element(s) having the sequence:

5'-GGTTTA-NNNN-AGTTCA (SEQ ID NO:2), wherein each N is independently selected from A, G, T or C, said method comprising contacting said cells with at least one isoform of LXR.

In accordance with a further embodiment of the present invention, there are provided methods of screening for RXR- and/or LXR-selective ligands, said method comprising:

(a) introducing a reporter construct and an LXR (or RXR) expression construct into a suitable host cell, wherein said reporter construct comprises an LXRE (or RXRE), operatively linked to a reporter gene, and (b) treating the modified host cell produced by step (a) with potential RXR- (or LXR-)specific ligand(s), and (c) identifying compound(s) which induce expression of said reporter.

The coincident expression pattern of LXRα and RXRα suggests these genes may have a role in adult physiology as was originally predicted for RXRα (Mangelsdorf et al., in *Nature* 345:224–229 (1990)). Accordingly, invention methods can be applied to the treatment of a wide variety of disease states in which RXR mediated processes are involved.

The invention will now be described in greater detail by reference to the following non-limiting examples.

EXAMPLE 1

Molecular Cloning of a Human LXRα

Sequential low-stringency screening (as described previously, see Mangelsdorf et al., (1990) supra) of a human liver λgt11 cDNA library with a 503 bp cDNA probe encoding the human RARα DNA-binding domain (i.e., the KpnI/SacI restriction fragment of hRARα, which includes the DNA-binding domain) led to the isolation of several potential nuclear receptor clones.

Positive clones were isolated, subcloned into pGEM vectors (Promega) restriction mapped, and sequenced by the dideoxy method with sequenase (US Biochemical) using both single-stranded and double-stranded DNA templates. Sequences were aligned and analyzed by the University of Wisconsin Genetics Computer Group programs (Devereux et al., supra). Several LXR clones were isolated; the longest, designated λHL1-1, contained a 2.8 kb insert that was subsequently subcloned into the EcoR1 site of pBluescript-KS (Stratagene). Because the size of this insert is identical to that of the vector and contains ~1.2 kb of 5' sequence that appears to be unrelated to the LXR cDNA, the first 1151 nucleotides of this clone were excised by EcoRV digestion at two restriction sites, one within the insert and the other in the multiple cloning site of the vector. The resultant DNA was religated and named pXR2ΔRV. The putative cDNA insert of pXR2ΔRV is 1680 bp (see SEQ ID NO:1) and contains the entire coding region of hLXRα as well as a potential polyadenylation signal sequence and 33 bases of the poly(A+) tail. Eighteen bp downstream from an in-frame termination codon at nucleotide 127 is the predicted translation start codon for LXRα at nucleotide 148. Translation from this ATG predicts an LXRα protein of 447 amino acids ($M_r$ 49,000) that has been confirmed by in vitro transcription/translation of the LXRα cDNA depicted in SEQ ID NO:1. This clone also contains 188 bp of 3' UTR which includes a canonical polyadenylation signal and a tract of 33 adenosines of the presumptive poly(A) tail. From these results, it can be concluded that this cDNA encodes the full-length LXRα protein.

Based on its initial isolation from the liver and its liver-rich expression pattern, this orphan receptor was designated LXRα.

Figure 1:
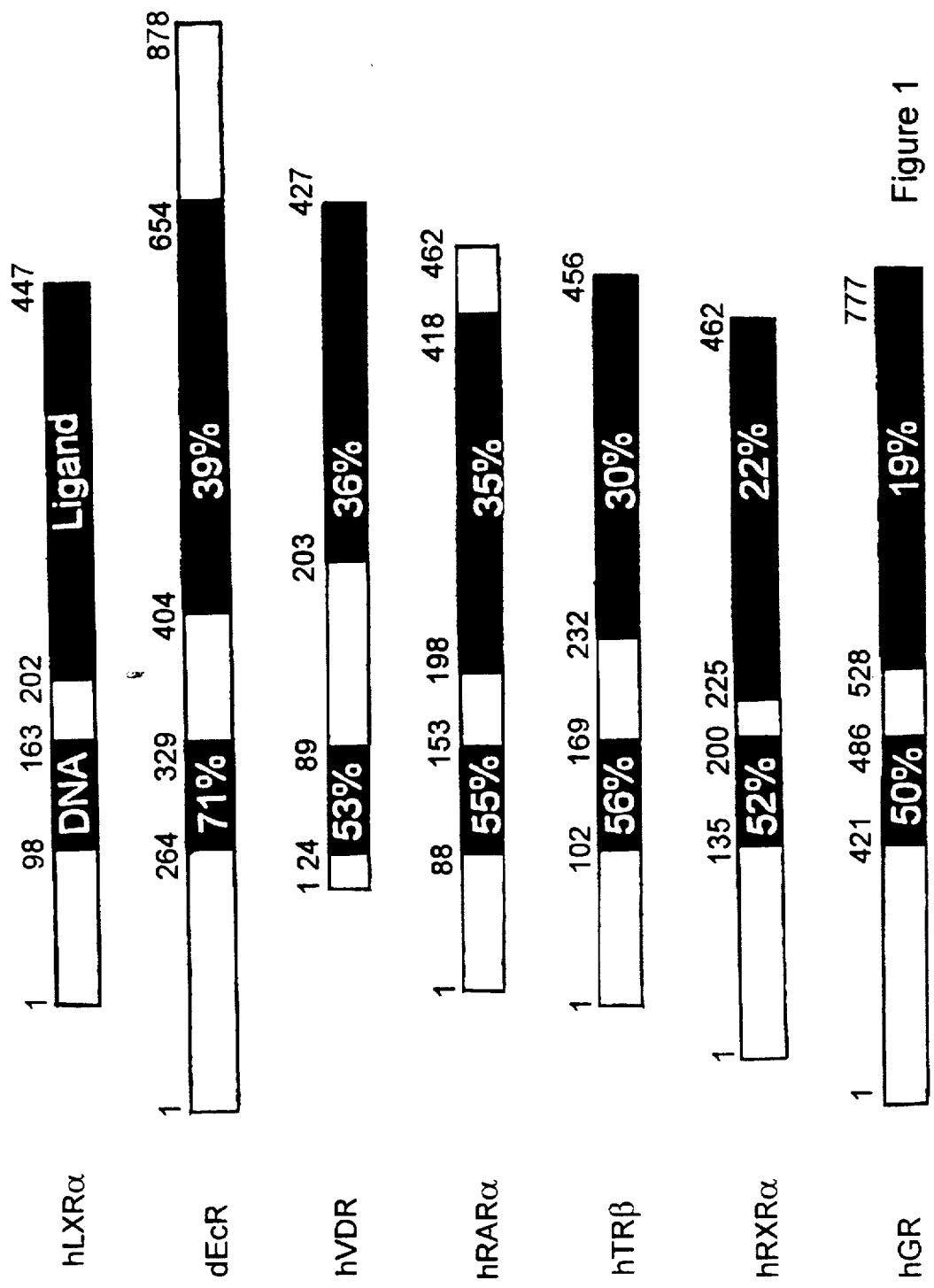
FIG. 1 presents an amino acid sequence comparison between human (h)LXRα and other members of the nuclear receptor superfamily. Sequence alignments were determined using the University of Wisconsin Genetics Computer Group programs (Devereux et al., in *Nucleic Acids Res.* 12:387–395 (1984)). Regions of significant similarity between hLXRα and other receptors are presented schematically as percent amino acid identify. dEcR, Drosophila ecdysone receptor (Koelle et al., in *Cell* 67:59–77 (1991)); hVDR, human vitamin D receptor (Baker et al., in *Proc. Natl. Acad. Sci. USA* 85:3294–3298 1988); hRARα, human retinoic acid receptor α (Giguèere et al., in *Nature* 330:624–629 (1987)); hTRμ, human thyroid hormone receptor μ (Weinberger et al., in *Nature* 324:641–646 (1986)); hRXRα, human retinoid X receptor α (Mangelsdorf et al., in *Nature* 345:224–229 (1990)); hGR, human glucocorticoid receptor (Hollenberg et al., in *Nature* 318:635–641 (1985)).

A comparison of the human LXRα orphan receptor with a number of other members of the nuclear receptor superfamily is depicted in FIG. 1. Human (h)LXRα shares closest identity with the Drosophila ecdysone receptor (dEcR), having a 71% similar DNA binding domain and 39% similar putative ligand binding domain. The degree of sequence identity of hLXRα with the known human receptors, however, is much less, but overall it is greatest with the human vitamin D receptor (hVDR). Interestingly, of the non-steroid subclass of receptors with known ligands, hLXRα has the lowest similarity to hRXRα (52% in the DNA binding domain, 22% in the ligand binding domain). From genomic Southern analysis, and preliminary evaluation of other LXRα-related cDNAs, it is noted that LXR likely constitutes a gene family with at least one other member.

EXAMPLE 2

Plasmids

Construction of wild-type receptor inserted into the expression vectors RSV and CMX, have been detailed elsewhere (Giguèere et al., in *Cell* 46:645–652 (1986); Umesono et al., in *Cell* 65:1255–1266 (1991); Mangelsdorf et al., (1990) supra). The hLXRα cDNA insert was excised from the plasmid pXR2ΔRV with Kpn1 and BamHI and ligated into the expression vectors RSV and CMX. Chimeric Gal4-receptor expression plasmids (e.g. CMX-GAL4-LXRα) were constructed by first ligating the GAL4 portion of pSG424 (Sadowski and Ptashne, in *Nucleic Acids Res.* 17:7539–7530 (1989)) into the HindIII/SacI sites of pCMX (Umesono et al., in *Cell* 65:1255–1266 (1991)) to create pCMX-GAL4. This vector contains the CMV promoter fused to the coding sequence for GAL4 (1–147), followed by inframe polylinker cloning sites and translational stop codons. The cDNAs encoding the ligand-binding domain (LBD) of each of the receptors were then ligated into the polylinker to create GAL4-LBD fusions.

The following receptor amino acid sequences were used for these constructions and their corresponding DNA sequences ligated into pCMX-GAL4:hLXRα 166–447, hRXRα 203–462 and hRARα 185–462.

Likewise, chimeric VP16-receptor expression plasmids were constructed by fusing the cDNA fragment encoding the 78 amino acid transactivation domain of VP16 (Triezenberg et al., in *Genes Dev.* 2:718–729 (1988)) in-frame to the cDNA encoding the desired nuclear receptor. The VP16-receptor fusions were engineered into CMX expression plasmids. Each chimera contains a 6–12 amino acid linker at the VP16-receptor fusion point to facilitate an in-frame junction. Kozak translational start sites (CACCATGG) were engineered into the 5-prime end of the VP16-receptor chimeras to provide strong initiator methionines. All fusion points and cloning sites were sequenced and the full-length proteins in vitro synthesized to insure sequence fidelity. Reporter plasmids for these studies were constructed by ligating the appropriate oligonucleotides into the HindIII site of the TK-LUC vector to create TK-LXRE-LUC, TK-MH100x4-LUC (Kang et al., in *J. Biol. Chem.* 268:9629–9635 (1993)), TK-DR4x2-LUC (Umesono et al., (1991) supra), TK-CRBPII-LUC (Mangelsdorf et al., (1991) supra), TK-βSRE-LUC (Sucov et al., in *Proc. Natl. Acad. Sci. USA* 87:5392–5396 (1990)). All constructs were verified by sequencing.

EXAMPLE 3

Cell Culture and Cotransfection Assays

CV-1 cells were maintained at 37° C., 5% $CO_2$ in DMEM containing 5% calf bovine serum (CBS). Transfections were performed in 8-well plates in media containing 5% dextran-charcoal stripped CBS by the calcium phosphate coprecipitation technique as described previously (Mangelsdorf et al., (1990) supra). Eight hours after transfections ligands were delivered to cells at $10^3$-fold dilutions (0.1% vol/vol of solvent in media). Retinoids (gifts from Marcus Boehm at Ligand Pharmaceuticals, Inc.) were manipulated under gold light and stored dark in ethanol or methanol under nitrogen gas at −80° C. Cells were harvested 36 hours after addition of ligand and analyzed for luciferase and β-galactosidase activity using a Dynatech microtiter plate Model ML3000 luminometer and a Model MR5000 spectrophotometer, respectively.

For most experiments, cotransfection of DNA into mammalian cells was accomplished with 50 ng reporter plasmid, 50 ng RSV- or CMX-βgal, 25 ng of each receptor expression plasmid and pGEM carrier to give 375 ng DNA/well. For controls, the empty CMX vector was used in place of the receptor cDNA. For the GAL4-receptor chimera experiments, 30 ng receptor and 80 ng of reporter plasmid were used. For GAL4 and VP16 chimera interaction assays, 30 ng of GAL4-LXRα and 15 ng of the VP16-RAR or -RXR were used along with 80 ng of the reporter plasmid. All transfection data points were normalized using an internal β-galactosidase marker (Mangelsdorf et al., (1990) supra) and represent the mean of duplicate or triplicate assays.

EXAMPLE 4

Northern Analysis

Murine poly(A)+ RNA used in these studies was prepared and assayed by Northern Analysis as described previously (Mangelsdorf et al., in *Genes Dev.* 6:329–344 (1992)). Equal amounts (10 μg) of poly(A)+RNA were loaded in each lane and verified by ethidium bromide staining. The DNA hybridization probe used on each blot was the 534 bp EcoR1 fragment of the pXR2ΔRV cDNA insert. This probe includes nucleotides 1147–1680 of the hLXRα cDNA and encodes part of the ligand binding domain and 3'-untranslated region of the clone. Autoradiography was for two days at −70° C. with intensifying screens.

Northern blot analyses were performed to determine the tissue distribution and developmental pattern of LXRα gene expression. Poly(A+) RNA isolated from a variety of adult rat tissues or from staged whole mouse embryos (gestation day 10.5 to 18.5) was size-fractionated, transferred to nylon filters, and hybridized with the hLXRα cDNA. The distribution of LXRα mRNA reveals an expression pattern similar to that of RXRα (Mangelsdorf et al., (1990) supra), with strong expression in metabolic organs such as liver, kidney, and intestine. The 1.9 kb LXRα message is also notably present in spleen and to a lesser extent in the adrenals. Analysis of expression during mouse development indicates low levels of LXRα are detected at embryonic day 13.5 and continue to increase in abundance through parturition.

EXAMPLE 5

Electrophoretic Mobility Shift Assays

For EMSA experiments, receptor proteins were generated using a coupled in vitro transcription/translation system according to the manufacturer's instructions (Promega). Sequences of double-stranded oligonucleotides were as shown in the figures and text and were synthesized with HindIII overhangs. Binding reactions were performed in a total volume of 20 μl consisting of 75 mM KCl, 20 mM Hepes, pH 7.4, 2 mM DTT, 7.5% glycerol, 0.1% NP-40, 2

MG poly (dI-dC) (Pharmacia), 40 pmol of a non-specific single-stranded oligonucleotide (for removal of non-specific binding in the lysates), and 2 μl of receptor lysates or unprogrammed (control) lysates. Reactions containing lysates and competing oligonucleotides were incubated for 30 minutes on ice followed by the addition of 40 fmol of $^{32}$P-labeled oligonucleotide probe (labeled by end-filling) and further incubated for 20 minutes at room temperature. Samples were then analyzed on 5% polyacrylamide gels run in 0.5X TBE buffer. For antibody supershifting experiments, 1 μl of anti-hRXRα antiserum (a gift from Jacki Dyck), or non-specific antiserum was added to the reactions after addition of the radiolabeled probe and incubated at room temperature for 10 minutes, followed by gel electrophoresis.

EXAMPLE 6

LXRα Transactivation by Retinoids

Figure 2A:
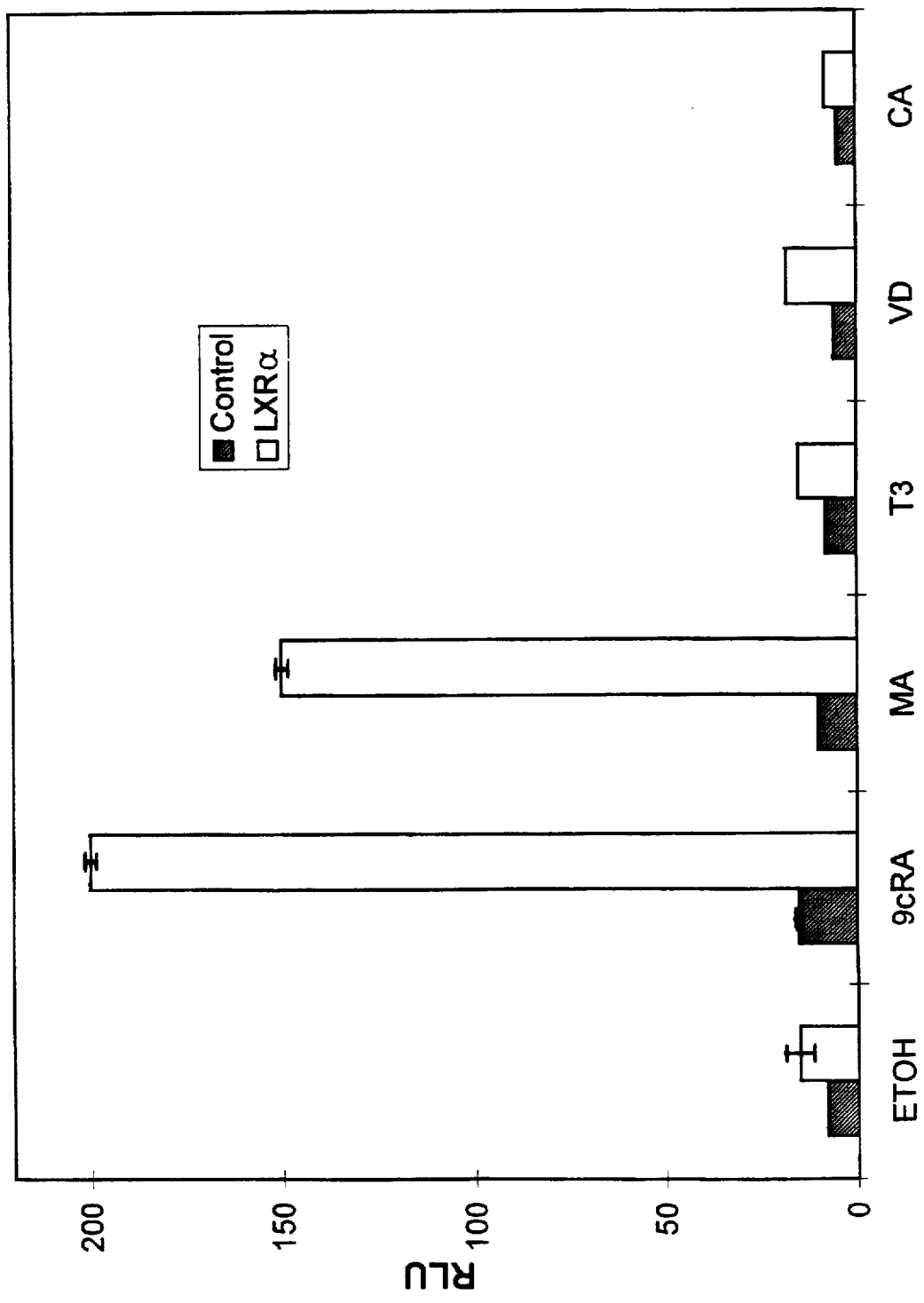
In FIG. 2a, CV1 cells were cotransfected with either a control plasmid (Control) or an expression plasmid for hLXRα, as indicated, in combination with the luciferase reporter plasmid TK-LXRE3-LUC and then incubated with various ligands (see below) or an ethanol control (ETOH).

To identify a potential ligand for the orphan receptor LXRα, a cell-based cotransfection screening assay similar to that used to successfully identify the RXR ligand (see Mangelsdorf et al., (1990) supra; Heyman et al., in Cell 68:397–406 (1992)) was employed. Initially an LXR responsive gene was unknown, therefore the preliminary experiments were designed to first identify an LXR-specific DNA binding sequence that could serve as an LXR responsive element (referred to as an LXRE). During the course of these experiments, a specific, high affinity DNA binding site for LXRα was discovered in the promoter sequence of ΔMTV, a promoter derived from the mouse mammary tumor virus LTR (see SEQ ID NO:6). This discovery suggested that the ΔMTV LXRE sequence could be transferred to a heterologous promoter, such as thymidine kinase (TK), and used with a luciferase (LUC) reporter gene for screening potential LXRα ligands. Thus, an assay system was established by transfecting CV-1 cells with an expression plasmid harboring the cDNA for LXRα and the luciferase reporter plasmid TK-LXRE3-LUC (see FIG. 2a). TK-LXRE3-LUC contains three copies of the LXRE defined herein; TK-CRBPII-LUC contains the RXRE from the rat CRBPII promoter (Mangelsdorf et al., (1991) supra)); TK-βRE-LUC contains the RAR response element from the mouse RARβ2 promoter (Sucov et al., (1990) supra). Luciferase activity is expressed in relative light units (RLU) and represents the mean of triplicate assays (±SEM) normalized to βgal as an internal standard. For the experiments summarized in panels 2a and 2c–2e), three different retinoid ligands that have previously been used to distinguish between retinoid receptor systems were used: $10^{-5}$M 9-cis retinoic acid (9cRA), which binds to both RXR and RAR (Heyman et al., (1992) supra; Levin et al., in Nature 355:359–361 (1992)); $10^{-5}$M TTNPB, which is RAR-specific (Mangelsdorf et al., (1990) supra); and $10^{-4}$M methoprene acid (MA), which is RXR-specific. The concentrations of other ligands used in (a) were $10^{-6}$M thyroid hormone (T$_3$), $10^{-6}$M 1,25-dihydroxyvitamin D$_3$ (VD), and 1 mM clofibric acid (CA).

In a comprehensive screen of several classes of compounds, it was found that LXRα activation is only induced by the presence of certain retinoid ligands. Remarkably, LXRα is strongly activated by both 9-cis retinoic acid (9cRA) and methoprene acid (MA), which have previously been shown to be RXR-specific ligands. The presence of both LXRα and retinoid is required to confer transactivation of the luciferase reporter gene containing the LXRE (compare "Control" to "LXRa" in FIG. 2a).

Figure 2B:
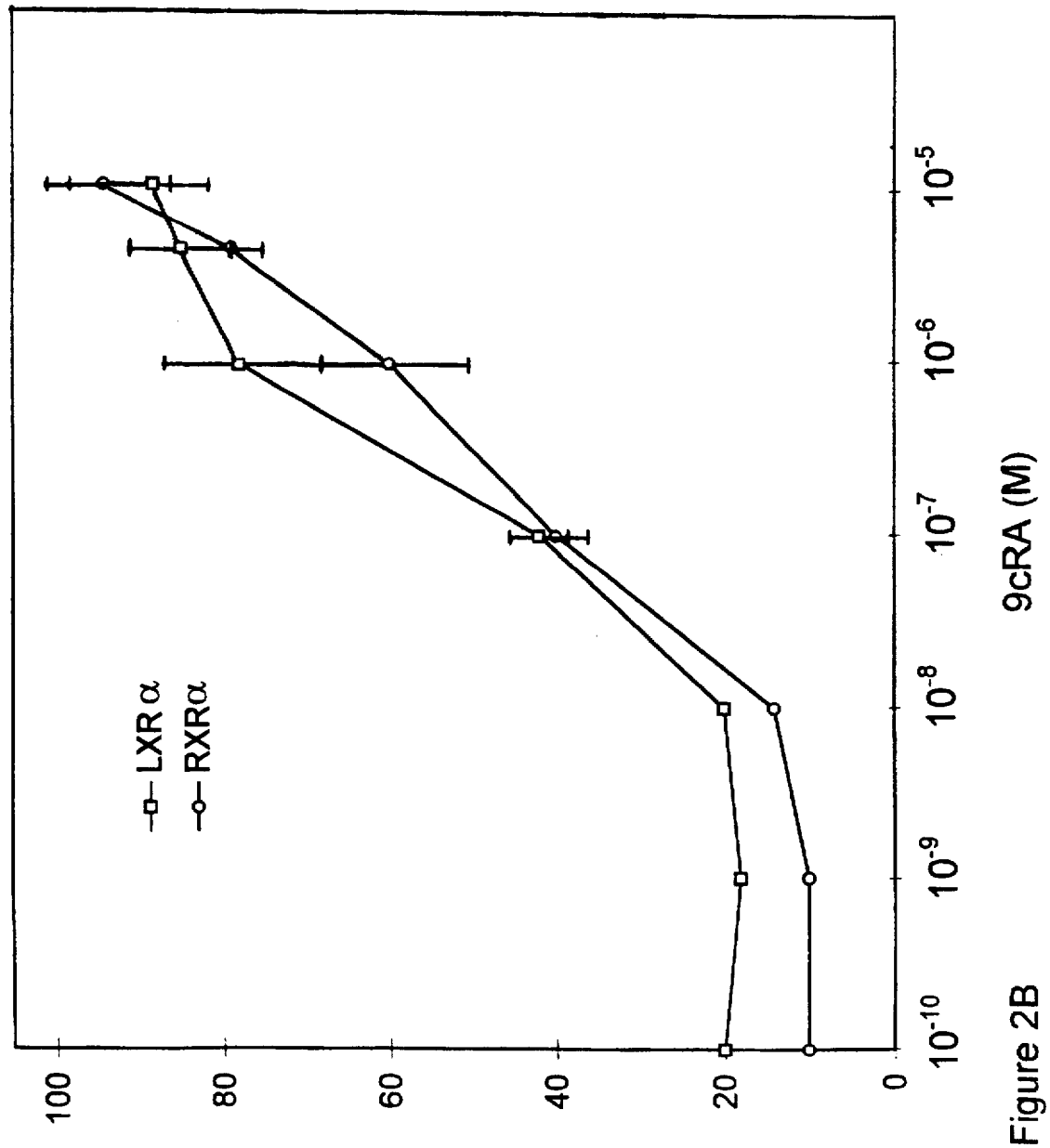
In FIG. 2b, LXRα and RXRα dose response to 9-cis retinoic acid is shown. CV1 cells were cotransfected with expression plasmids for hLXRα (squares) or hRXRα (circles) and the reporter plasmids TK-LXRE3-LUC or TK-CRBPII-LUC, respectively, and then incubated with increasing concentrations of 9-cis retinoic acid.

Since these results are similar to the activation specificity of RXRα, a side-by-side comparison of dose responses to 9cRA was performed with LXRα and RXRα and their cognate response elements. As shown in FIG. 2b, both LXRα and RXRα show nearly identical concentration-dependent activation profiles in response to 9cRA. Similar dose responses were observed with several other RXR-specific ligands, including methoprene acid and LG69 (Kurokawa et al., in Nature 371:528–531 (1994)). These results suggest the existence of a distinct pathway of gene regulation mediated by LXRα and 9cRA.

EXAMPLE 7

Figure 2C:
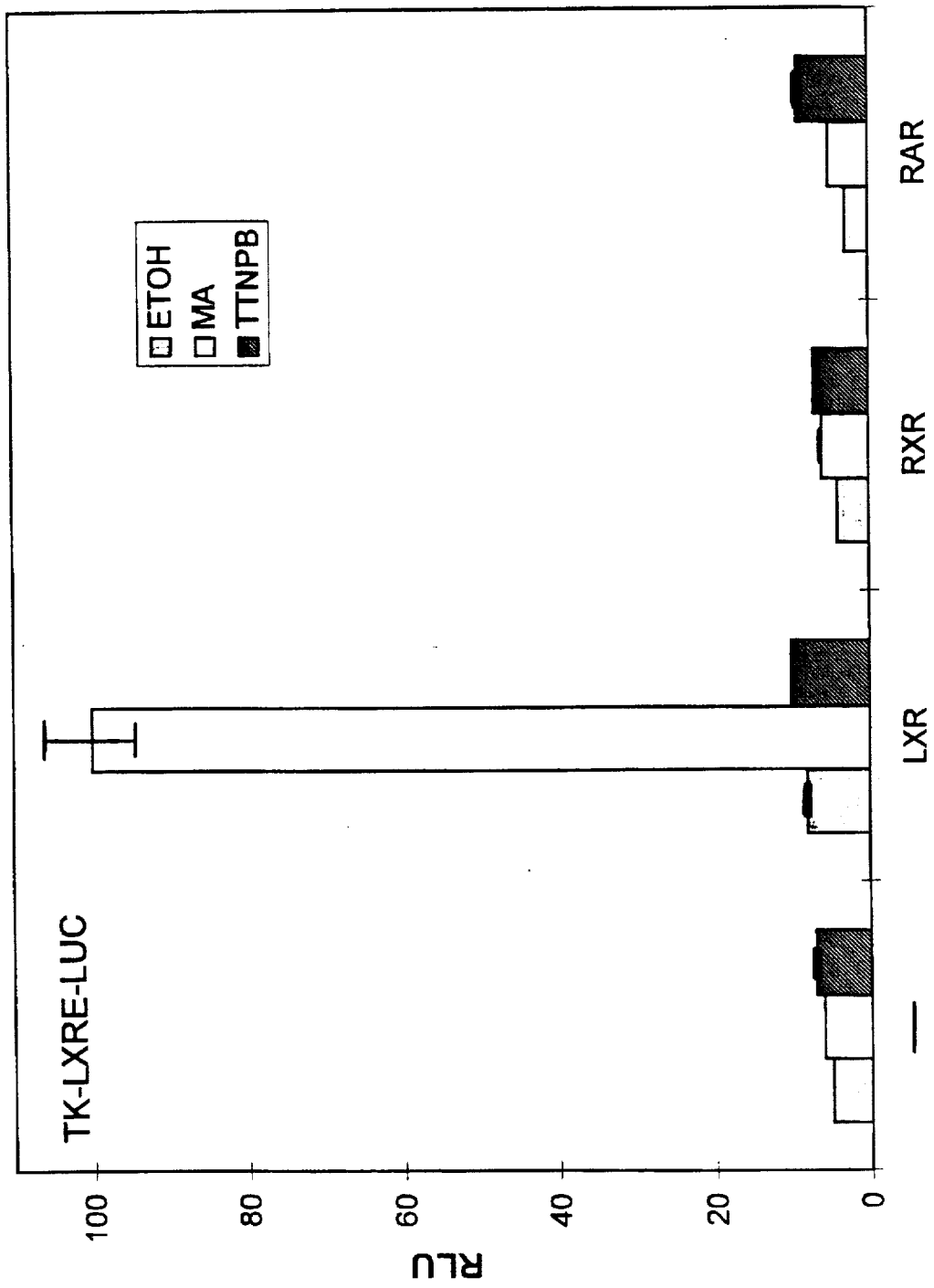
In FIGS. 2c–2e, LXRα, RXRα, and RARα activation by retinoids is shown to be response element specific. Thus, CV1 cells were cotransfected with either a control plasmid (−) or expression pladmids for hLXRα, hRXRα, or hRARα in combination with reporter plasmids TK-LXRE3-LUC (see FIG. 2c), TK-CRBPII-LUC (see FIG. 2d), or TK-μRE-LUC (see FIG. 2e) and then incubated with various retinoid ligands (see below) or an ethanol control.
Figure 2D:
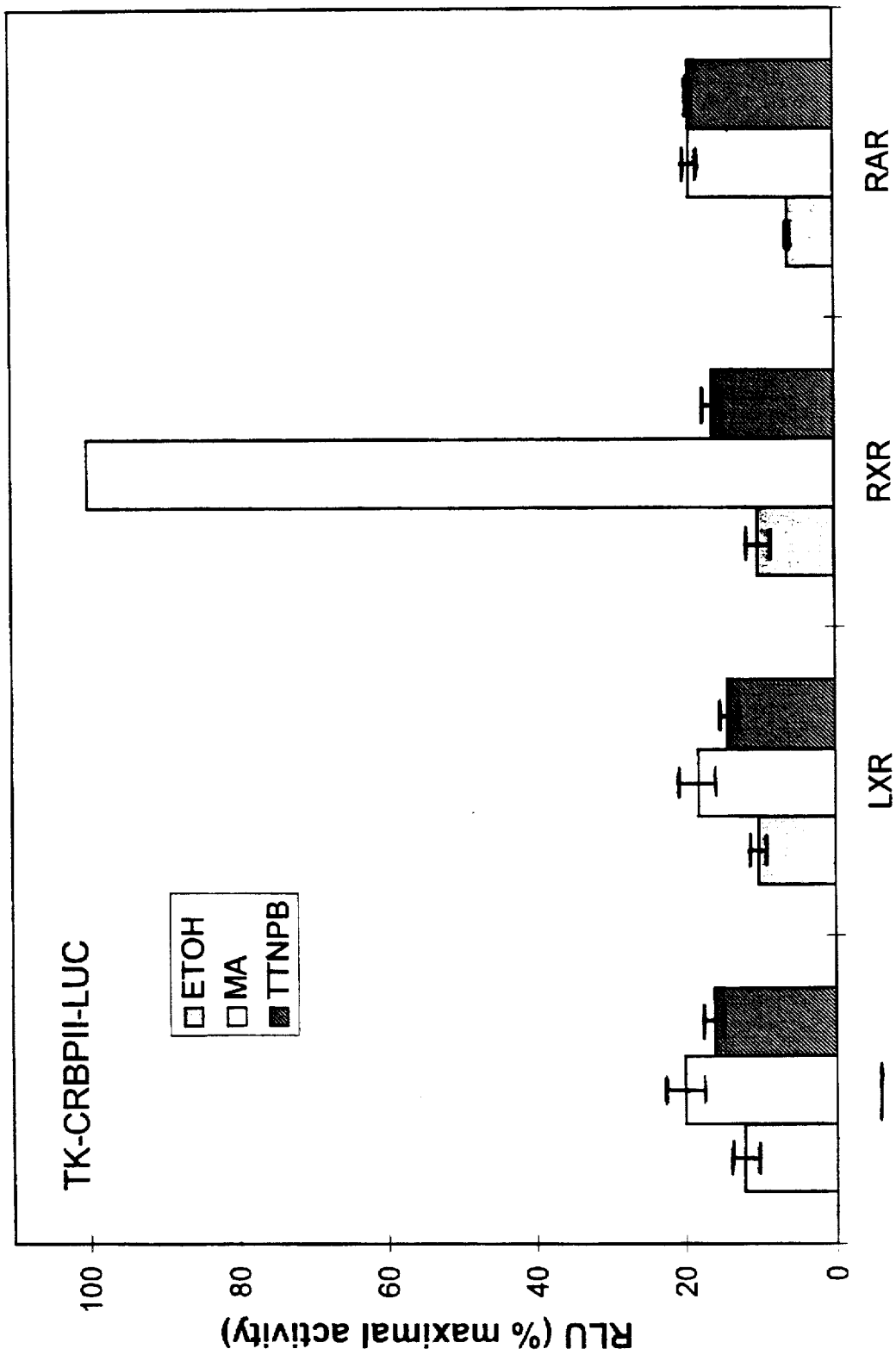
Figure 2E:
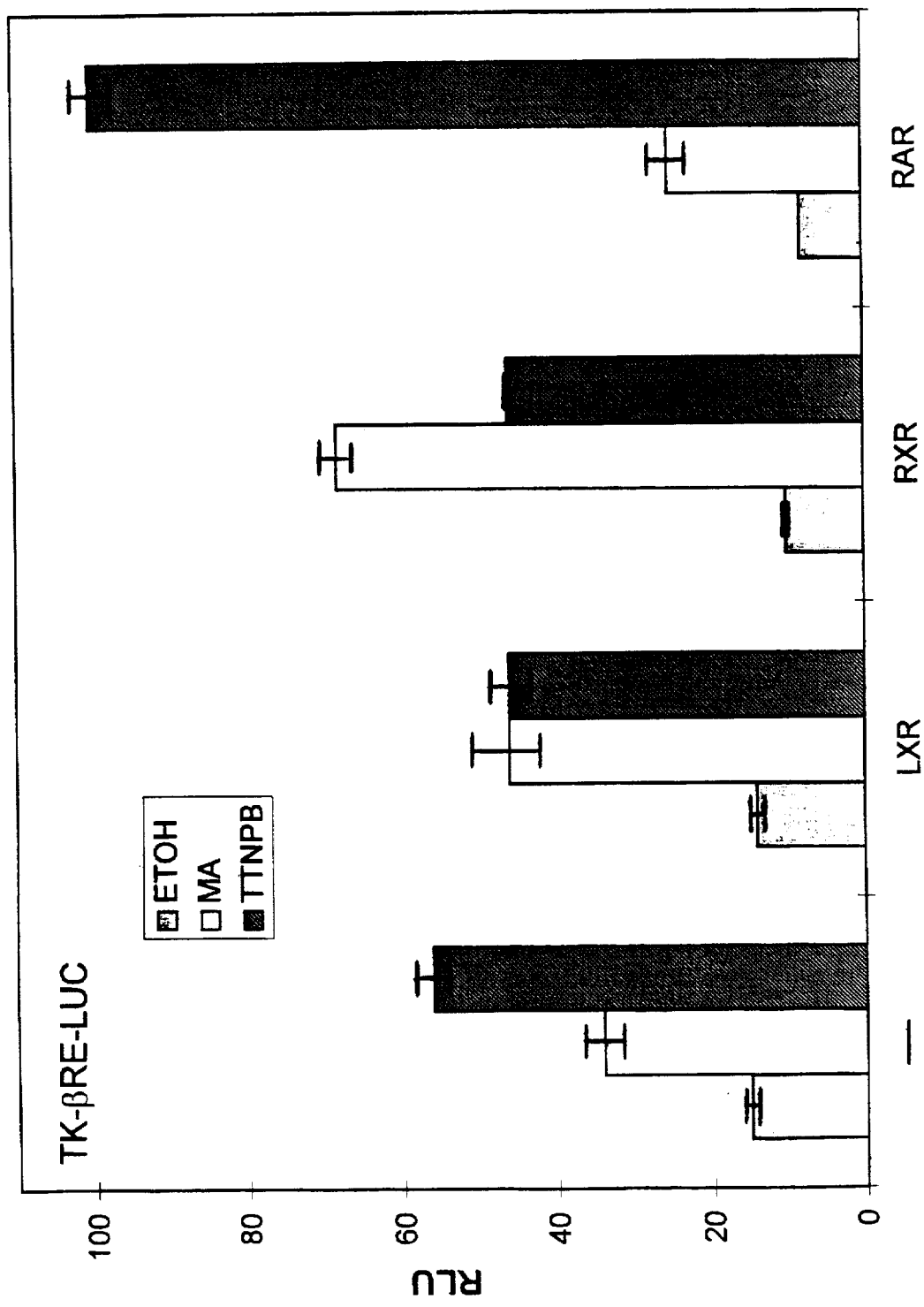

Three Distinct Retinoid Response Pathways To further demonstrate that the LXR retinoid response is authentic and distinguishable from the pathways previously described by the RXR and RAR receptor systems, cotransfection experiments were performed to directly compare the three receptor systems by using receptor-specific ligands and response elements (see FIGS. 2c–e). For these experiments, the two retinoid ligands, methoprene acid (MA) and (E)-4-[2-(5,6,7,8-tetrahydro-5,5,8,8-tetramethyl-2-napthalenyl)-1-propenyl]benzoic acid (TTNPB), which have previously been shown to be uniquely specific for RXR and RAR, respectively (Mangelsdorf et al., (1990) supra; Kurokawa et al., (1994) supra) were used. Expression plasmids for the three receptors (LXRα, RXRα, and RARα) were cotransfected into CV1 cells along with luciferase reporters containing their respective response elements and tested for ligand-dependent activation. In the absence of any response element, the empty reporter plasmid TK-LUC conferred no receptor or ligand dependent transactivation. However, as shown above, in the presence of the RXR-specific ligand, methoprene acid, LXRα strongly activates transcription from the LXRE-containing reporter (see FIG. 2c). In contrast, the RAR-specific ligand TTNPB had no effect on the activation of LXRα. Significantly, neither RXRα nor RARα were able to substitute for LXRα in mediating LXRE dependent transactivation, even in the presence of the cognate ligands.

FIG. 2d and 2e demonstrate that the retinoid responsiveness of LXRα is specific to the LXRE, and cannot also be mediated through other retinoid response elements. Previously, a retinoid response element (that is specific for the RXR homodimer) has been identified from the rat CRBPII promoter (Mangelsdorf et al., (1991) supra). When this RXR response element (RXRE) is placed into the promoter of the luciferase reporter plasmid (TK-CRBPII-LUC), there is a marked response to the RXR ligand, methoprene acid (see FIG. 2d). This response occurs in the presence of RXRα, but not RARα or LXRα. It is noteworthy that even though these cells contain low levels of endogenous RXR, the RXR homodimer response requires the transfection of additional RXR.

In similar experiments, when a reporter plasmid containing an RAR response element (TK-SRE-LUC) is used, the retinoid response is limited to RAR and RXR and their cognate ligands (FIG. 4e). The response to TTNPB occurs through an RXR/RAR heterodimer, whereas the response to methoprene acid occurs through an RXR homodimer which can also weakly bind to this element (zhang et al., in Nature 358:587–591 (1992); Kurokawa et al., in Nature 371:528–531 (1994)). This activation occurs even in the absence of transfected RAR or RXR, confirming the existence of endogenous retinoid receptors. As has been previously reported, the addition of exogenous RARα or RXRα accordingly increases the respective retinoid response. Importantly, there is no further increase in activation when LXRα is transfected into these cells. These data clearly demonstrate that LXRα has a retinoid response cis element specificity that is distinctly unique from RXR and RAR. Furthermore, the LXR response occurs in the absence of transfected RXR or RAR. Taken together, these results distinguish the human LXRα as a novel mediator of retinoid action.

EXAMPLE 8

LXRα Forms a Functional Heterodimer with RXRα

The data presented above suggest two possible explanations to account for the specific activation of LXRα by retinoids. One possibility is that LXRα is functioning in a fashion similar to other receptors. In this scenario, LXRα transactivation through an LXRE might be mediated by an LXR homodimer or an RXR/LXR heterodimer in which LXR binds the ligand. However, based on the RXR-like specificity of the retinoid response, another plausible explanation is that LXRα is not directly bound and activated by these retinoids, but instead is an obligatory heterodimeric partner of endogenous RXR, and that retinoid binding (and thus, transactivation) requires the presence of RXR. In either case, it is clear that receptor binding and transactivation through the LXRE is uniquely dependent on the presence of LXRα, since both the RXR homodimer and RXR/RAR heterodimer fail to activate on the LXRE (see FIG. 2c).

Figure 3A:
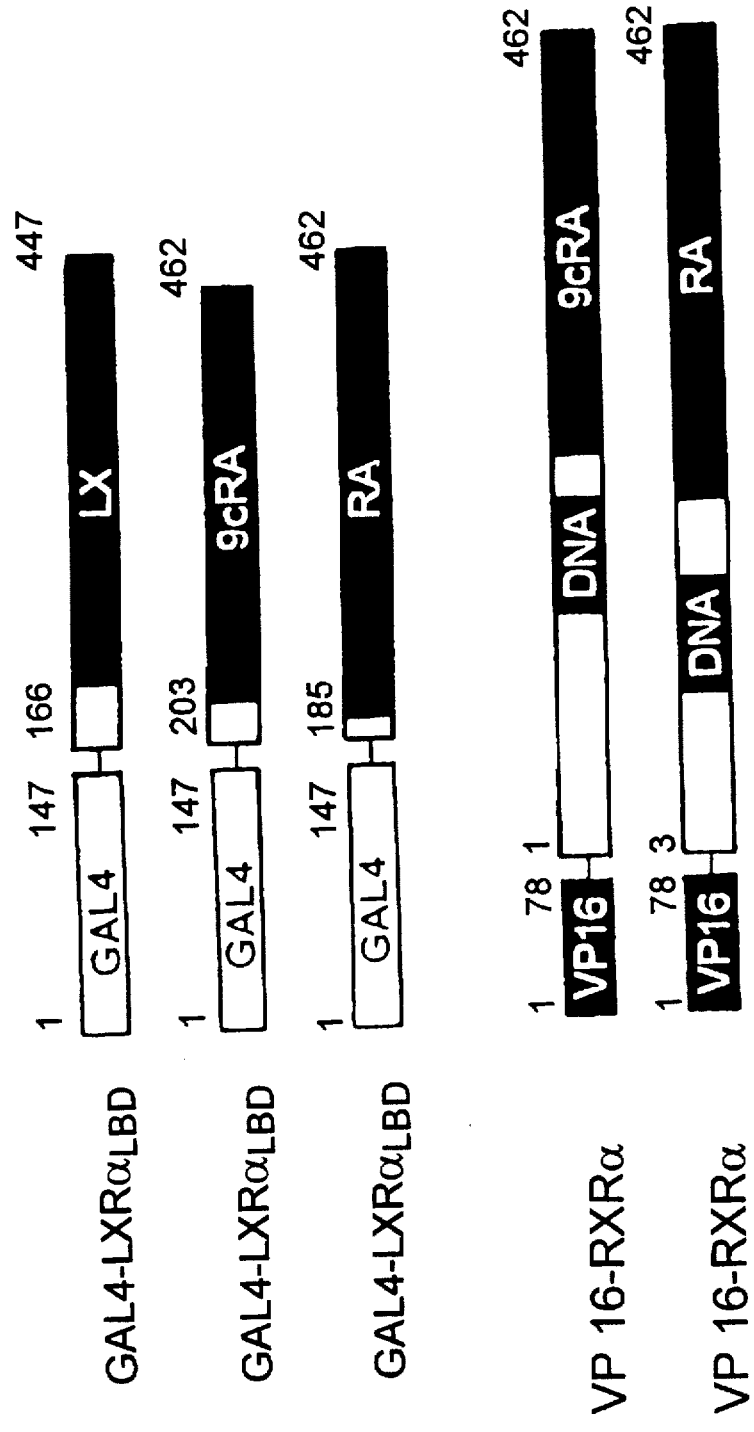
FIG. 3A provides a schematic representation of GAL4 and VP16 hybrid proteins used in these experiments. The amino acid sequences from each parent protein used to construct the hybrid receptors are shown above each schematic.
Figure 3B:
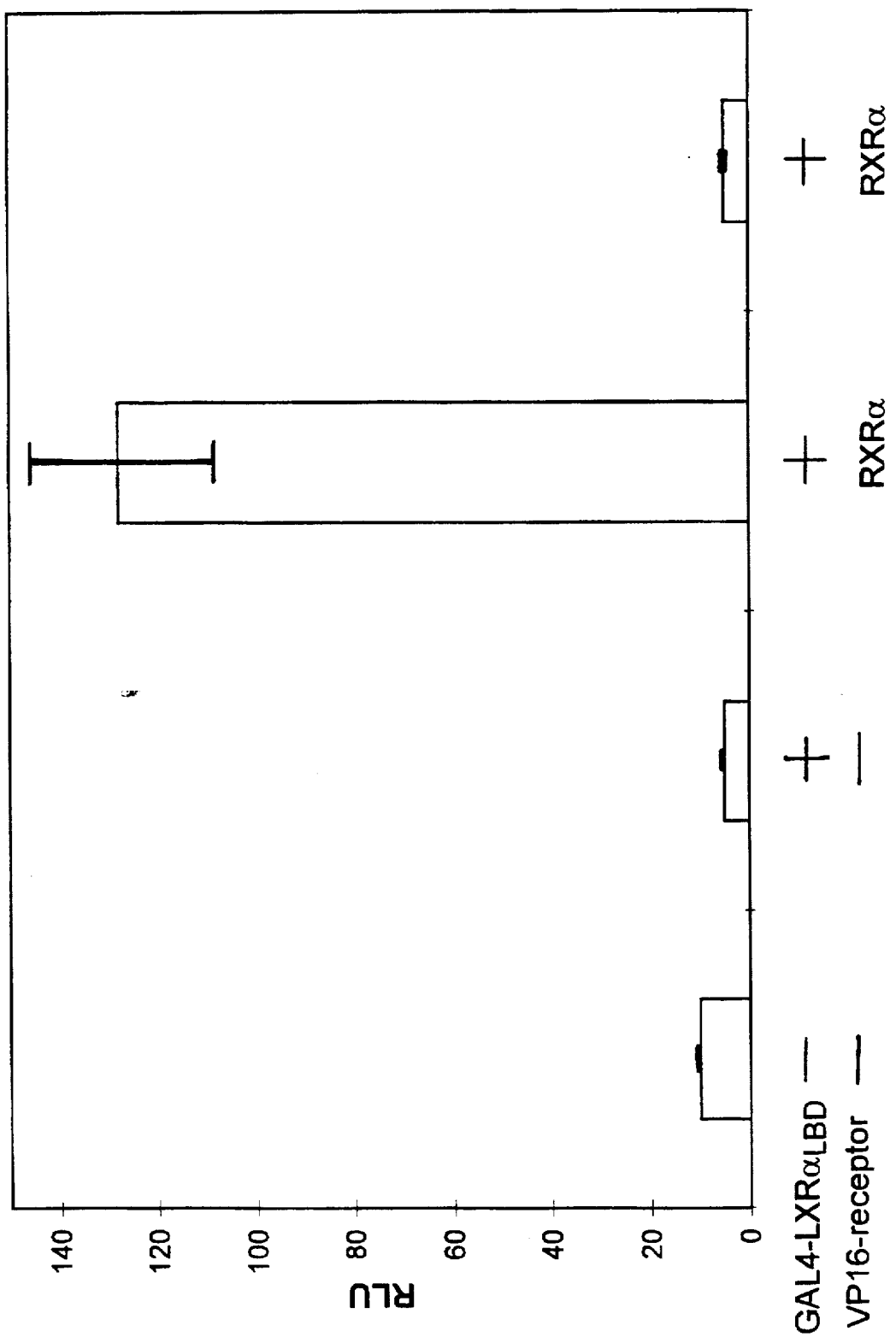
FIG. 3B illustrates the fact that transactivation of the GAL4-LXRα construct requires the presence of VP16-RXRα, but not VP16-RARα, in the mammalian two hybrid system. In negative control experiments, none of the VP16-receptors alone are able to confer transactivation.

To test the feasibility of these two hypotheses, the possibility of a heterodimeric interaction between LXRα and one of the other receptors was examined. For these studies, a mammalian version of the two hybrid system originally described for the detection of protein-protein interactions in yeast (Fields and Song, in *Nature* 340:245–246 (1989)) was employed. In this strategy, the ligand binding domain of one receptor (i.e., LXRα) is fused to the DNA binding domain of GAL4, creating a hybrid protein (GAL4-LXRα, FIG. 3a) that can bind to specific upstream activation sequences (UAS$_G$), but which lacks a constitutive transactivation domain and therefore cannot by itself activate transcription of a luciferase reporter (FIG. 3b). The use of the LXRα ligand binding domain as the "bait" in these experiments is based on previous studies which have localized a strong dimerization interface in the ligand binding domain of other nuclear receptors (Perlmann et al., (1993) supra; and Kurokawa et al., *Genes Dev.* 7:1423–1435 (1993)).

To screen for receptors that may interact with LXRα, the candidate receptors were fused to the 78 amino acid transactivation domain of VP16. Each VP16-receptor chimera (FIG. 3a) was cotransfected along with GAL4-LXRα into CV-1 cells (FIG. 3b). In the presence of two receptors capable of dimerization, the VP16 transactivation domain is brought into functional proximity with the GAL4 DNA binding sequences, which in turn permits activation of the promoter driving luciferase expression. As is clearly demonstrated in FIG. 3b, only the VP16 hybrid protein containing RXRα, but not RARα, is able to induce transcription in the presence of GAL4-LXRα. Similar VP16 hybrids of the vitamin D and thyroid hormone receptors are unable to confer transactivation. These experiments demonstrate a specific interaction between LXRα and RXRα and are strong evidence that these two receptors form a functional heterodimer in vivo.

EXAMPLE 9

GAL4-Receptor Hybrids Define Ligand Binding Specificity

To address the possibility that the retinoid response elicited by LXRα was through the direct interaction of ligand with the putative ligand binding domain of LXRα, ligand activation experiments were performed with the GAL4-receptor hybrids. Previous studies have shown that the ligand binding domains of nuclear receptors contain ligand-dependent activation domains (Nagpal et al., in *Cell* 70:1007–1019 (1992)). Thus, when a nuclear receptor ligand binding domain is fused to the DNA binding domain of GAL4, this hybrid transcription factor alone can confer ligand-dependent transactivation of a UAS$_G$-containing reporter (Nagpal et al., in *EMBO J.* 12:2349–2360 (1993)). Such heterologous system provides an effective means for directly assaying receptor/ligand interactions, even in the presence of endogenous wild-type receptors.

Figures 1, 3C:
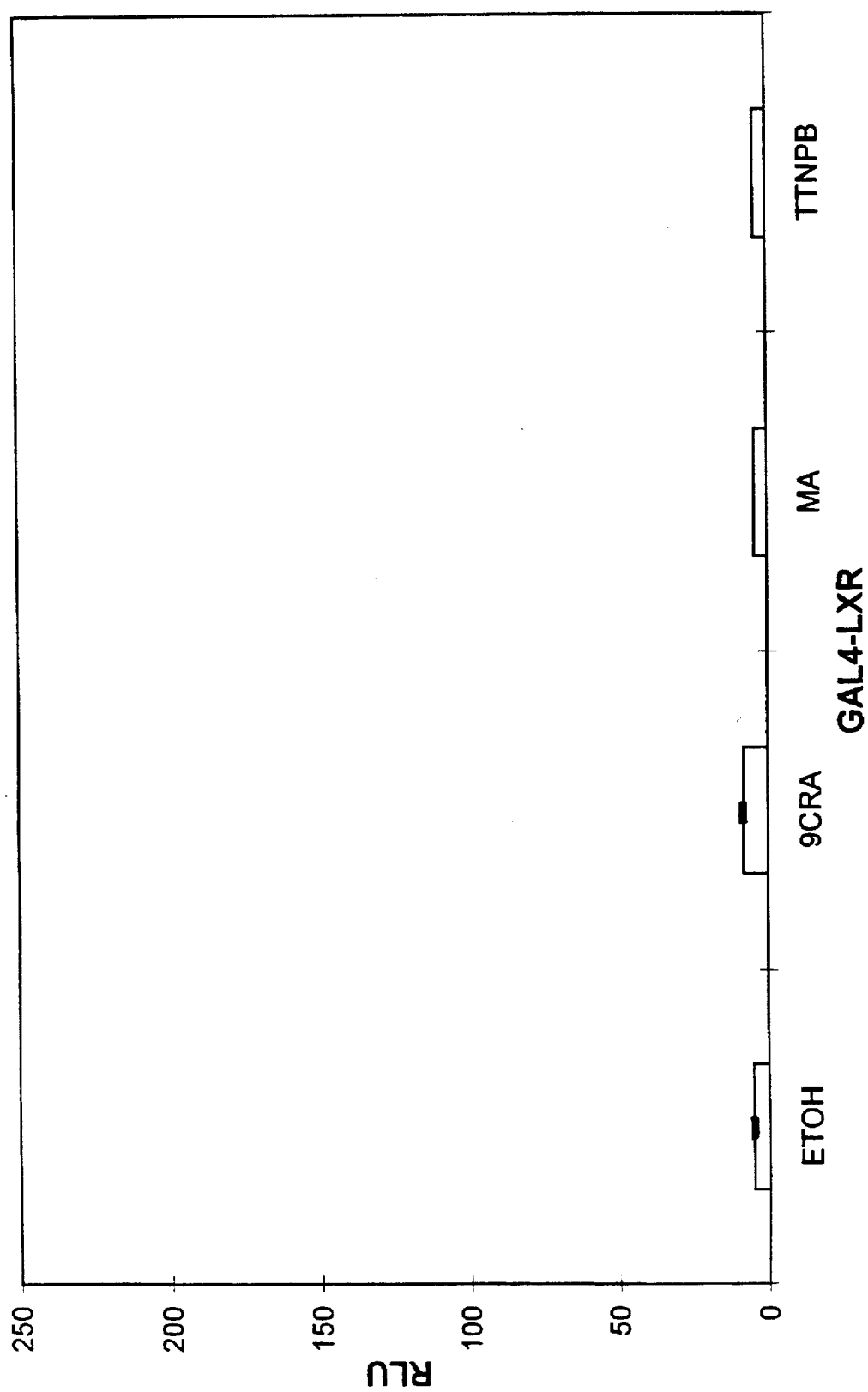
FIG. 3C illustrates the ligand specificity of the GAL4-receptor chimeras. Thus, it is demonstrated that retinoid responsiveness can be conferred through the ligand binding domains of RXR and RAR, but not LXR. In both 3B and 3C, CV1 cells were cotransfected as described previously with CMX vectors driving expression of the indicated hybrid proteins and the reporter plasmid TK-MH100x4-LUC, which contains four copies of the GAL4 DNA upstream activation sequence.

As shown in FIG. 3c, the chimeric constructs GAL4-RXR and GAL4-RAR confer ligand inducible transactivation that accurately mimics the cognate ligand specificity of wild-type receptor proteins: 9cRA activates both RXR and RAR, methoprene acid only activates RXR, and TTNPB specifically activates RAR. In contrast, no activation is seen with the GAL4-LXR chimera in the presence of these same ligands. These results indicate that retinoid receptor ligands cannot directly interact with the LXRα ligand binding domain when evaluated under similar conditions that permit their interaction with RXR and RAR. Furthermore, the specificity of 9cRA and methoprene acid for RXR, taken together with the heterodimerization studies, are strong evidence that the LXRα retinoid response requires the presence of RXRα.

EXAMPLE 10

LXR/RXR Heterodimers Bind and Activate Through the LXRE

Figures 2, 3C:
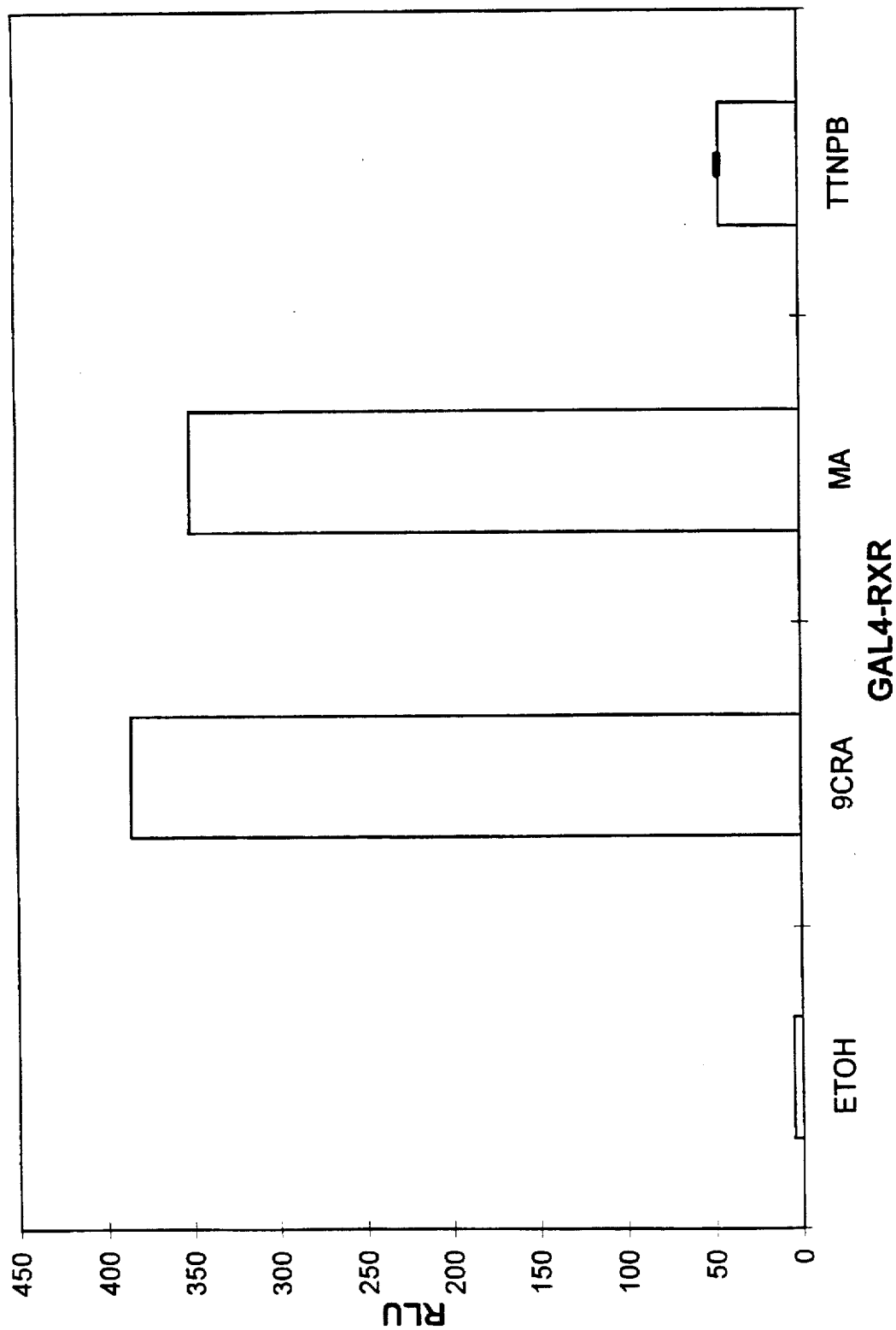
FIG. 2 collectively demonstrates that retinoids specifically induce LXRα.
Figures 3, 3C:
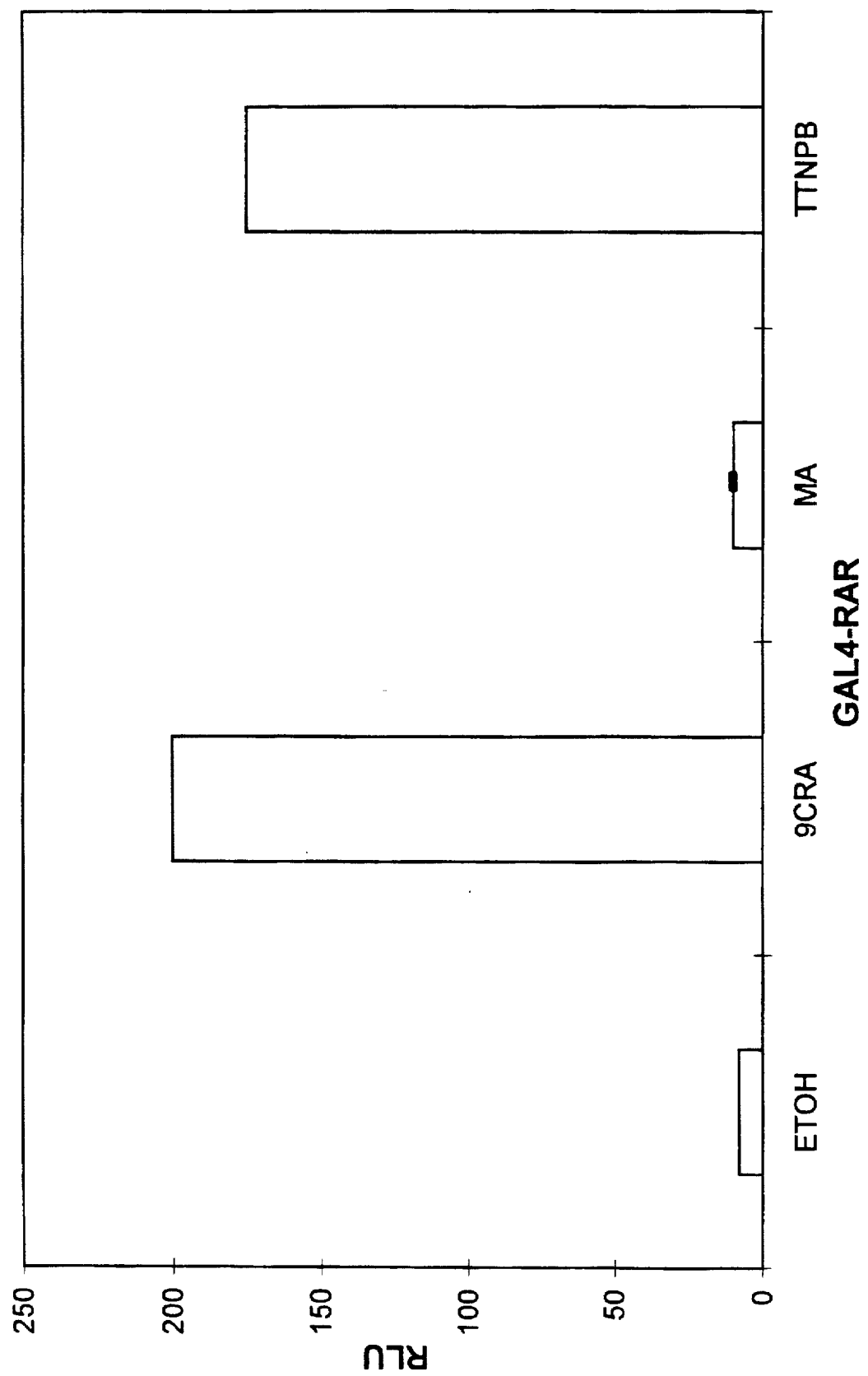
FIG. 3 collectively demonstrates that the putative ligand binding domain of LXRα contains a functional, RXR-specific heterodimerization domain, but not a functional retinoid binding domain.

The previous experiments suggest the existence of an LXR/RXR heterodimer as the mediator of retinoid signaling through a unique retinoid response element, referred to as the LXRE. This element was originally identified in the 5' regulatory region of ΔMTV, a promoter derived from the mouse mammary tumor virus LTR that is routinely used in conjunction with heterologous response elements to drive receptor-specific expression of reporter genes (Hollenberg and Evans, in *Cell* 55:899–906 (1988)). In the context of the reporter gene, ΔMTV promoter identified a region of 30 nucleotides (see SEQ ID N):) that when removed from ΔMTV-LUC abolished retinoid activation by LXRα. As demonstrated in FIG. 2, this sequence can be transferred to the TK-LUC vector and confer full LXRα activation by retinoids. As has been shown to be the case with all other nuclear receptor response elements, increasing the number of LXREs in the reporter plasmid coincidentally increases hormone responsiveness.

To test whether this sequence was specifically bound by an LXR/RXR heterodimer, electrophoretic mobility shift assays were performed using in vitro synthesized receptor proteins and $^{32}$P-labelled LXRE probe. LXRα and RXRα do not bind to the LXRE probe individually, but when mixed together a strong protein-DNA complex is formed. This complex is supershifted in the presence of RXRα-specific antisera, but not in the presence of a non-specific antisera. These results are consistent with the conclusion that only the LXR/RXR heterodimer is capable of high affinity binding to the LXRE.

Figure 4:
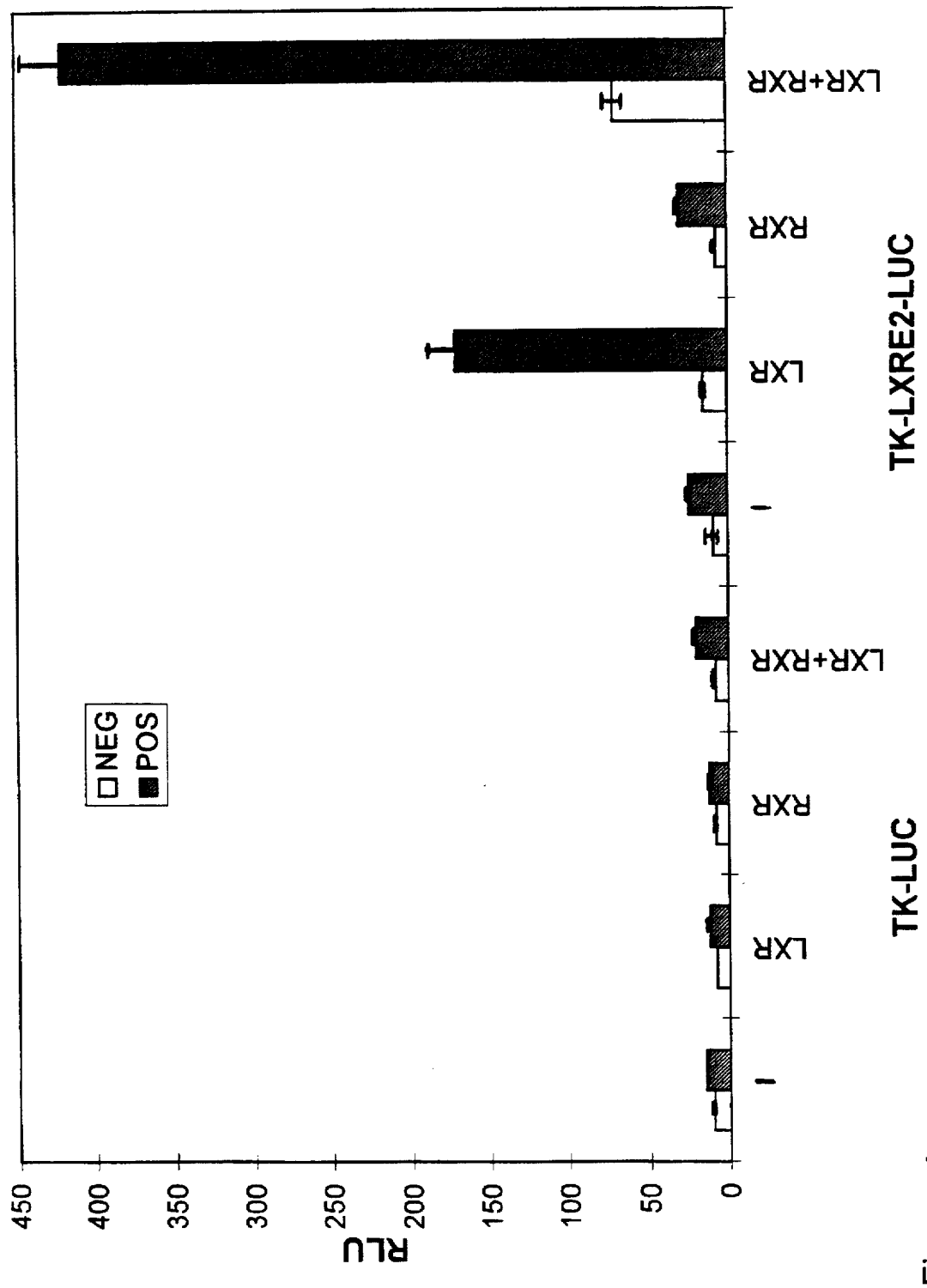
FIG. 4 demonstrates that the LXRE is a functional, high affinity binding site for LXR/RXR heterodimers.
Figure 5A:
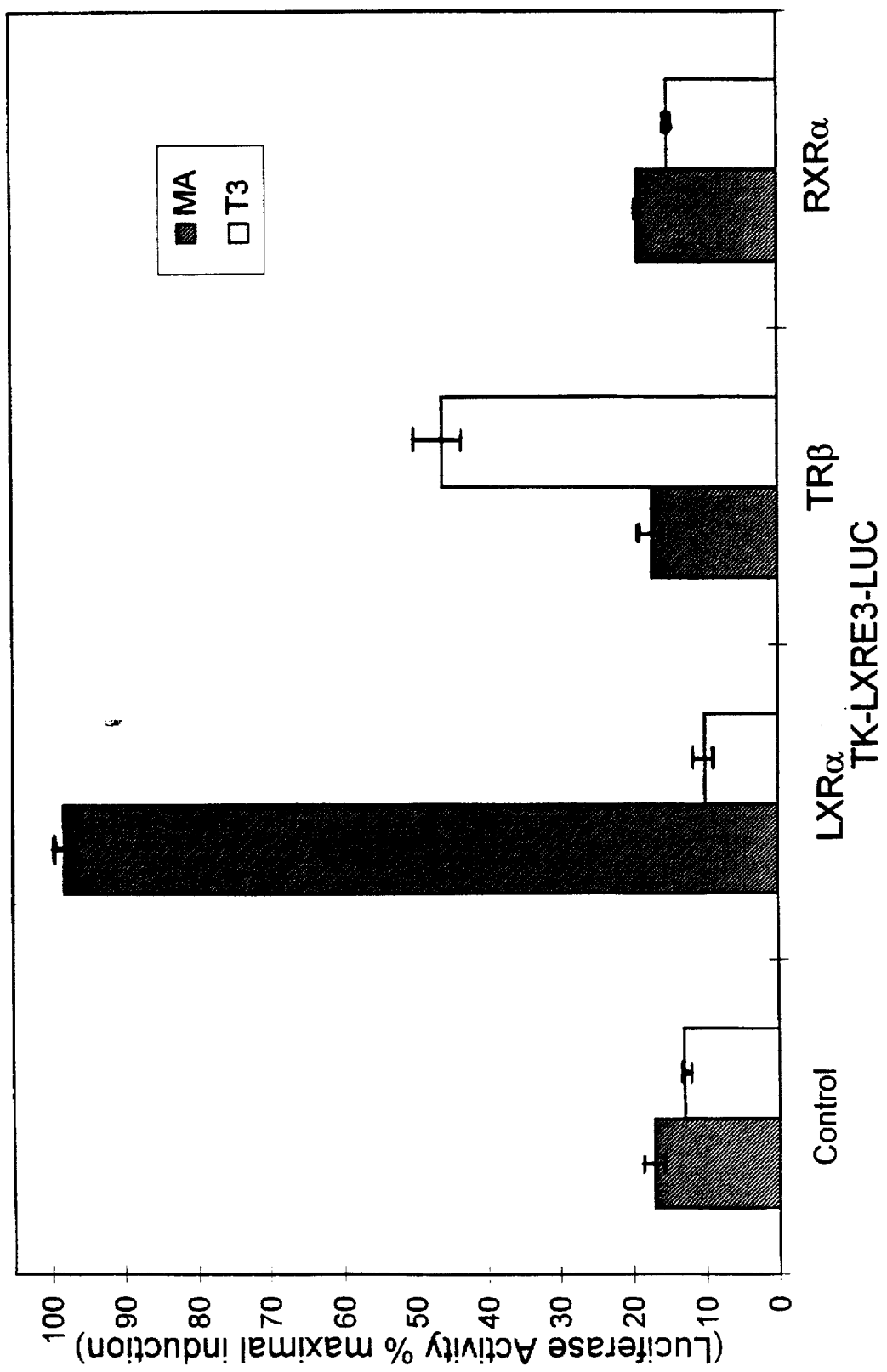
FIG. 5 illustrates the transactivation of LXRα TRμ, or RXRα on an LXRE (TK-LXRE3-LUC) or a canonical DR4 response element (TK-DR4x2-LUC) reporter. Like the canonical DR4 element, other known thyroid hormone response elements such as the MHC-TRE (Izumo and Mahdavi, in *Nature* 334:539–542 (1988)) and the FAS-TRE (Amy et al., in *Biochem. J.* 271:675–679 (1990)) also demonstrate high affinity LXRα binding, but are not retinoid responsive. Cotransfections and luciferase assays were performed as described with reference to FIG. 2; ligands were added at $10^{-4}$M methoprene acid (MA) or $10^{-6}$M thyroid hormone ($T_3$). Luciferase activity is expressed as (±SEM of triplicate assays).
Figure 5B:
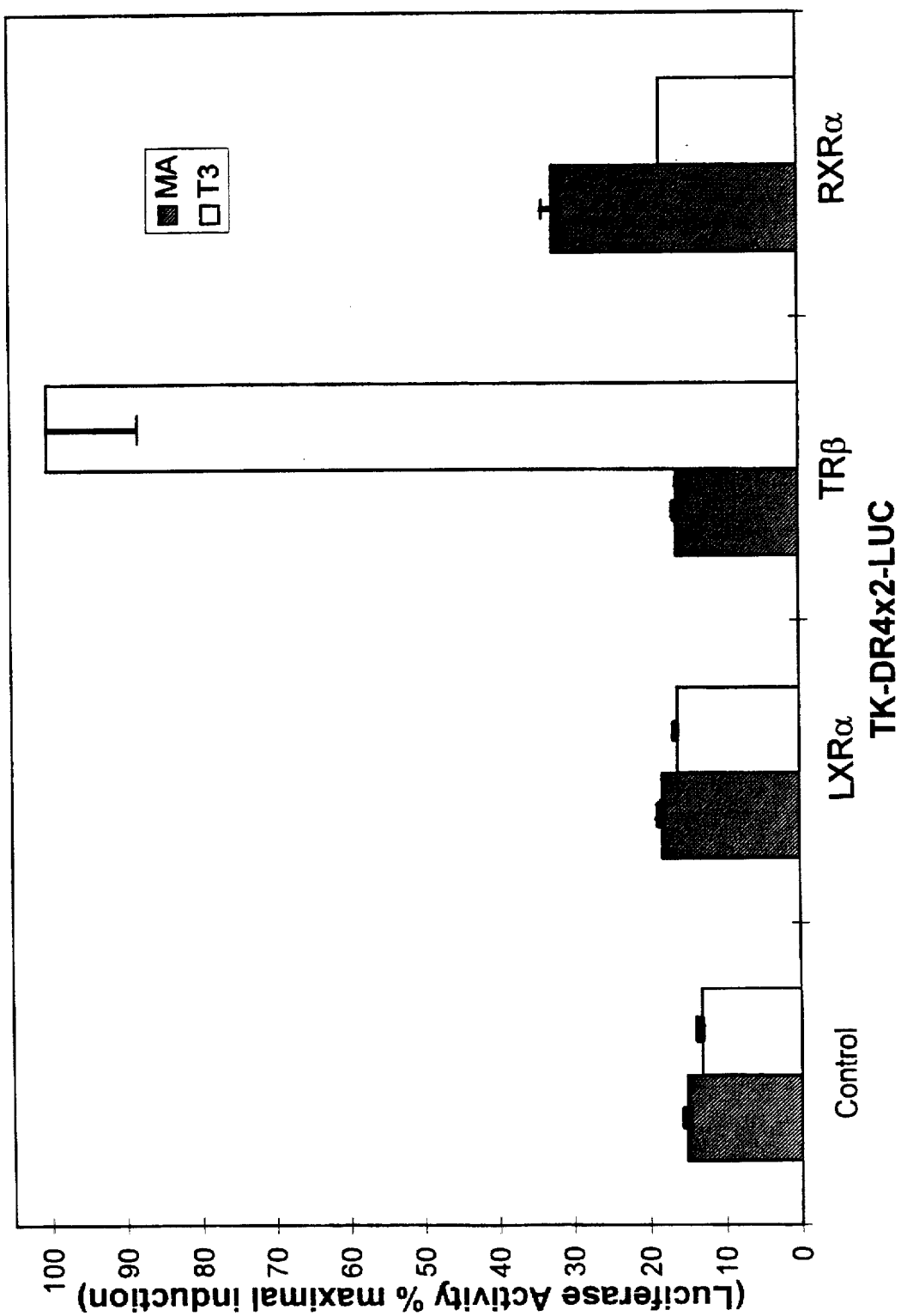

To demonstrate the functionality of the LXR/RXR heterodimer, an experiment was performed by cotransfecting both LXRα and RXRα with the LXRE reporter in the presence of the RXR-specific ligand, methoprene acid (see FIG. 4). Thus, expression plasmids for hLXRα, hRXRα, or no receptor (−) were cotransfected into CV1 cells in combination with the reporter plasmids TK-LUC or TK-LXRE2-LUC as indicated. Cells were then incubated with ethanol control (−) or $10^{-4}$M methoprene acid (+) and assayed for luciferase activity as described above. TK-LXRE2-LUC contains two copies of the LXRE. In experiments in which LXR and RXR plasmids were cotransfected together the ratio of the two expression plasmids was 1:0.1 (25 ng hLXRα:2.5 ng hRXRα). In all other experiments were LXR and RXR were added alone, the amount of each receptor expression plasmid was 25 ng.

As demonstrated above, the addition of LXRα alone gives a marked ligand response, whereas RXRα alone gives no response. However, when both LXRα and RXRα are added together, there is a dramatic synergistic increase in both basal and retinoid responsive activity. The LXR/RXR heterodimer must be exquisitely sensitive to retinoid, because under the conditions these experiments were performed, even the addition of one-tenth the amount of exogenous RXR markedly increases the LXR-dependent response. This response has been observed in several mammalian cell types. From these experiments, it can be concluded that the presence of endogenous RXR in these cells (Titcomb et al., in *Mol. Endocrinol* 8:870–877 (1994) ) is responsible for the ability of LXRα, when added alone, to confer retinoid responsiveness. This conclusion is consistent with the ability of endogenous RXR to also function as a heterodimeric partner for RAR and other nuclear hormone receptors. The important difference in this case is that RXR does not play the role of a silent partner, but rather takes on the role of the active receptor partner.

EXAMPLE 11

LXRE is a Novel DR4 Retinoid Response Element

Previously it has been shown that the heterodimers formed between RXR and other nuclear receptors can bind and activate through DNA response elements that are direct repeats of the core sequence AGGTCA spaced by 1 to 5 nucleotides (designated as DR1 to DR5; reviewed by (Mangelsdorf et al., (1994) supra; Kastner et al., in *Vitamin A in health and disease*, R. Blomhoff, ed. (New York: Marcel Dekker, Inc.) 189–238 (1994); Giguèere, V., *Endocr. Rev.* 15:61–79 (1994)). Inspection of the LXRE sequence in SEQ ID NO:6 reveals the presence of two degenerate hexad sequences spaced by four nucleotides that resemble the canonical direct repeat of AGGTCA half-sites.

The configuration of the LXRE into a putative direct repeat spaced by four nucleotides (i.e., DR4) was examined by performing a competition analysis with ten different mutant LXRE oligos in which individual pairs of nucleotides were systematically changed to cytosine (C) or guanine (G) in the region within and flanking the DR4 motif. The ability of mutant LXREs to compete with the labelled native LXRE probe was analyzed using the gel mobility shift assay. Mutant oligos with substitutions within either half-site of the DR4 motif fail to compete with native LXRE for binding to the LXR/RXR heterodimer, even at 50-fold molar excess. In contrast, LXRE oligos with similar substitution mutations in the spacer and flanking regions are able to compete well for binding to LXR/RXR. Furthermore, the introduction or substraction of a single nucleotide into the spacer region (thereby creating a DR5 or DR3 motif, respectively) resulted in oligos that fail to competitively bind the LXRE.

The data presented above suggest that the minimal LXRE is a DR4-type response element. To further investigate this possibility, a series of perfect AGGTCA direct repeat oligos, spaced by 1 to 5 nucleotides (DR1–5), were used to compete with labelled LXRE for binding the LXR/RXR heterodimer. Only the DR4 oligo is observed to compete as well as native LXRE for binding to LXR/RXR, even at a 10-fold molar excess. Since DR4 sequences are known to bind RXR/ thyroid hormone receptor heterodimers and function as potent thyroid hormone response elements, it was of interest to know if LXRα could also activate through these DR4 elements. Surprisingly, LXRα activation is specific only to the LXRE, and is not functional on a canonical DR4 thyroid hormone response element.

In independent experiments, it has also been demonstrated that the LXR/RXR can bind, but is completely inactive, on several other DR4 elements that are known to be thyroid hormone responsive as well. Interestingly, the LXRE is reciprocally a very poor thyroid hormone response element, in spite of the fact that the RXR/thyroid hormone receptor heterodimer binds to this sequence with high affinity. These experiments suggest that DNA binding alone is insufficient to permit transactivation. Thus, the LXRE represents a novel DR4 motif that can distinguish between two hormonal pathways.

While the invention has been described in detail with reference to certain preferred embodiments thereof, it will be understood that modifications and variations are within the spirit and scope of that which is described and claimed.

---

That which is claimed is:

1. An isolated nucleic acid comprising a retinoid-inducible response element wherein said response element has the sequence:

5'-GGTTTA-AATA-AGTTCA; SEQ ID NO:4.

2. An isolated nucleic acid comprising a retinoid-inducible response element wherein said response element has the sequence:

5'-GGTTTA-AATA-AGTTCA-$N_1N_2$; SEQ ID NO:5, wherein $N_1$ is A or T, and $N_2$ is C or G.

3. An isolated nucleic acid comprising a retinoid-inducible response element wherein said response element has the sequence:

5'-CTTGCGGTTCCCAG-GGTTTA-AATA-AGTTCA; SEQ ID NO:6.

4. An isolated nucleic acid comprising a retinoid-inducible response element wherein said response element has the sequence:

5'-CTTGCGGTTCCCAG-GGTTTA-AATA-AGTTCA-$N_1N_2$; SEQ ID NO:7, wherein $N_1$ is A or T, and $N_2$ is C or G.

5. A retinoid-inducible response element according to any one of claims 1–4, wherein said response element selectively binds LXR-RXR heterodimer(s).

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 447 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

-continued

| | | | | | | | | | | | | | | |
|---|---|---|---|---|---|---|---|---|---|---|---|---|---|---|
| Met 1 | Ser | Leu | Trp | Leu 5 | Gly | Ala | Pro | Val | Pro 10 | Asp | Ile | Pro | Pro 15 | Ser |
| Ala | Val | Glu | Leu 20 | Trp | Lys | Pro | Gly | Ala 25 | Gln | Asp | Ala | Ser 30 | Ser | Gln Ala |
| Gln | Gly | Gly 35 | Ser | Ser | Cys | Ile | Leu 40 | Arg | Glu | Ala | Arg 45 | Met | Pro | His |
| Ser | Ala 50 | Gly | Gly | Thr | Ala 55 | Gly | Val | Gly | Leu | Glu 60 | Ala | Ala | Glu | Pro Thr |
| Ala 65 | Leu | Leu | Thr | Arg 70 | Ala | Glu | Pro | Pro | Ser 75 | Glu | Pro | Thr | Glu | Ile Arg 80 |
| Pro | Gln | Lys | Arg | Lys 85 | Lys | Gly | Pro | Ala | Pro 90 | Lys | Met | Leu | Gly 95 | Asn Glu |
| Leu | Cys | Ser | Val 100 | Cys | Gly | Asp | Lys | Ala 105 | Ser | Gly | Phe | His | Tyr 110 | Asn Val |
| Leu | Ser | Cys 115 | Glu | Gly | Cys | Lys | Gly 120 | Phe | Phe | Arg | Arg | Ser 125 | Val | Ile Lys |
| Gly | Ala 130 | His | Tyr | Ile | Cys 135 | His | Ser | Gly | Gly | His 140 | Cys | Pro | Met | Asp Thr |
| Tyr 145 | Met | Arg | Arg | Lys | Cys 150 | Gln | Glu | Cys | Arg | Leu 155 | Arg | Lys | Cys | Arg Gln 160 |
| Ala | Gly | Met | Arg | Glu 165 | Glu | Cys | Val | Leu | Ser 170 | Glu | Glu | Gln | Ile 175 | Arg Leu |
| Lys | Lys | Leu | Lys 180 | Arg | Gln | Glu | Glu | Glu 185 | Gln | Ala | His | Ala | Thr 190 | Ser Leu |
| Pro | Pro | Arg 195 | Arg | Ser | Ser | Pro | Pro 200 | Gln | Ile | Leu | Pro | Gln 205 | Leu | Ser Pro |
| Glu | Gln 210 | Leu | Gly | Met | Ile | Glu 215 | Lys | Leu | Val | Ala | Ala 220 | Gln | Gln | Gln Cys |
| Asn 225 | Arg | Arg | Ser | Phe | Ser 230 | Asp | Arg | Leu | Arg | Val 235 | Thr | Pro | Trp | Pro Met 240 |
| Ala | Pro | Asp | Pro | His 245 | Ser | Arg | Glu | Ala | Arg 250 | Gln | Gln | Arg | Phe | Ala His 255 |
| Phe | Thr | Glu | Leu 260 | Ala | Ile | Val | Ser | Val 265 | Gln | Glu | Ile | Val | Asp 270 | Phe Ala |
| Lys | Gln | Leu 275 | Pro | Gly | Phe | Leu | Gln 280 | Leu | Ser | Arg | Glu | Asp 285 | Gln | Ile Ala |
| Leu | Leu 290 | Lys | Thr | Ser | Ala | Ile 295 | Glu | Val | Met | Leu | Leu 300 | Glu | Thr | Ser Arg |
| Arg 305 | Tyr | Asn | Pro | Gly | Ser 310 | Glu | Ser | Ile | Thr | Phe 315 | Leu | Lys | Asp | Phe Ser 320 |
| Tyr | Asn | Arg | Glu | Asp 325 | Phe | Ala | Lys | Ala | Gly 330 | Leu | Gln | Val | Glu | Phe Ile 335 |
| Asn | Pro | Ile | Phe 340 | Glu | Phe | Ser | Arg | Ala 345 | Met | Asn | Glu | Leu | Gln 350 | Leu Asn |
| Asp | Ala | Glu 355 | Phe | Ala | Leu | Leu | Ile 360 | Ala | Ile | Ser | Ile | Phe 365 | Ser | Ala Asp |
| Arg | Pro 370 | Asn | Val | Gln | Asp | Gln 375 | Leu | Gln | Val | Glu | Arg 380 | Leu | Gln | His Thr |
| Tyr 385 | Val | Glu | Ala | Leu | His 390 | Ala | Tyr | Val | Ser | Ile 395 | His | His | Pro | His Asp 400 |
| Arg | Leu | Met | Phe | Pro 405 | Arg | Met | Leu | Met | Lys 410 | Leu | Val | Ser | Leu | Arg Thr 415 |
| Leu | Ser | Ser | Val | His | Ser | Glu | Gln | Val | Phe | Ala | Leu | Arg | Leu | Gln Asp |

```
                        420                      425                      430
           Lys  Lys  Leu  Pro  Pro  Leu  Leu  Ser  Glu  Ile  Trp  Asp  Val  His  Glu
                          435                      440                      445
```

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:2:

GGTTTANNNN AGTTCA                                                                           16

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:3:

GGTTTANNNN AGTTCANN                                                                         18

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:4:

GGTTTAAATA AGTTCA                                                                           16

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide ( x i ) SEQUENCE DESCRIPTION: SEQ ID NO:5:

GGTTTAAATA AGTTCANN                                                                         18

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide (  x  i  ) SEQUENCE DESCRIPTION: SEQ ID NO:6:

CTTGCGGTTC CCAGGGTTTA AATAAGTTCA 30

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Oligonucleotide (  x  i  ) SEQUENCE DESCRIPTION: SEQ ID NO:7:

CTTGCGGTTC CCAGGGTTTA AATAAGTTCA NN 32